US012679813B2

(12) United States Patent
Yamagami et al.

(10) Patent No.: US 12,679,813 B2
(45) Date of Patent: Jul. 14, 2026

(54) TRIAZINE COMPOUND SALT, CRYSTAL FORM THEREOF, AND PRODUCTION METHOD THEREFOR

(71) Applicant: TANABE PHARMA CORPORATION, Osaka (JP)

(72) Inventors: Takafumi Yamagami, Osaka (JP); Tomofumi Setsuta, Osaka (JP); Yoshihiro Sugiura, Osaka (JP); Naoko Ueda, Osaka (JP)

(73) Assignee: TANABE PHARMA CORPORATION, Osaka (JP)

( * ) Notice: Subject to any disclaimer, the term of this patent is extended or adjusted under 35 U.S.C. 154(b) by 465 days.

(21) Appl. No.: 18/025,932

(22) PCT Filed: Sep. 15, 2021

(86) PCT No.: PCT/JP2021/033901

§ 371 (c)(1),
(2) Date: Mar. 13, 2023

(87) PCT Pub. No.: WO2022/059700

PCT Pub. Date: Mar. 24, 2022

(65) Prior Publication Data

US 2023/0365513 A1 Nov. 16, 2023

(30) Foreign Application Priority Data

Sep. 15, 2020 (JP) ................................ 2020-154875

(51) Int. Cl.
*C07D 253/07* (2006.01)

(52) U.S. Cl.
CPC ........ *C07D 253/07* (2013.01); *C07B 2200/13* (2013.01)

(58) Field of Classification Search
CPC .................................................. C07D 253/07
See application file for complete search history.

(56) References Cited

U.S. PATENT DOCUMENTS

| | | | | |
|---|---|---|---|---|
| 6,288,234 | B1 | 9/2001 | Griffin | |
| 10,029,993 | B2 * | 7/2018 | Ushirogochi ........ | C07D 471/04 |
| 10,329,263 | B2 * | 6/2019 | Ushirogochi ........ | C07D 471/04 |
| 2008/0103142 | A1 | 5/2008 | Goldstein et al. | |
| 2011/0015173 | A1 | 1/2011 | Florjancic et al. | |
| 2011/0152240 | A1 | 6/2011 | Haddach et al. | |
| 2012/0165309 | A1 | 6/2012 | Takahashi et al. | |
| 2015/0011535 | A1 | 1/2015 | Heckel et al. | |
| 2017/0044115 | A1 | 2/2017 | Ushirogochi et al. | |
| 2018/0312503 | A1 | 11/2018 | Sakakibara et al. | |
| 2024/0009201 | A1 | 1/2024 | Slingsby et al. | |

FOREIGN PATENT DOCUMENTS

| | | | |
|---|---|---|---|
| JP | 2010-502668 | A | 1/2010 |
| JP | 2012-533553 | A | 12/2012 |
| JP | 2013-512903 | A | 4/2013 |
| JP | 2016-526563 | A | 9/2016 |
| JP | 2017-81911 | A | 5/2017 |
| WO | WO 99/64051 | A1 | 12/1999 |
| WO | WO 2010/092962 | A1 | 8/2010 |
| WO | WO 2015/163427 | A1 | 10/2015 |
| WO | WO 2017/069226 | A1 | 4/2017 |
| WO | WO 2022/093714 | A1 | 5/2022 |
| WO | WO 2023/002407 | A2 | 1/2023 |

OTHER PUBLICATIONS

Berge et al (1977) : Journal of Pharmaceutical Sciences, vol. 66, No. 1, pp. 1-19.*

Hirayama, "Organic Compound Crystal Preparation Handbook", Principles and Knowhow., vol. 25, Jul. 2008, pp. 18-23, pp. 38-65 (33 pages total) with English translation of part of 13.

International Preliminary Report on Patentability and Written Opinion of the International Searching Authority dated Mar. 21, 2023 for Application No. PCT/JP2021/033901.

International Search Report dated Nov. 22, 2021 for Application No. PCT/JP2021/033901.

Ministry of Health and Welfare Pharmaceutical and Medical Safety Bureau Director of Examination Management Division, "Guidelines on Residual Solvent of Pharmaceutical Products", Iyakushin, Table 2, 1998, 12 pages total, with English translation of part of D12.

Registry, "Stereosearch", STN CAS Registry No. 1643919-88-3, Jan. 27, 2015 ([retrieved on Nov. 10, 2021]), 1 page.

Wermuth, "The Practice of Medicinal Chemistry", last vol. Technomics, Inc., Table 34.1, 1999, pp. 347-365 (21 pages total), with partial English translation.

Partial Supplementary European Search Report for European Application No. 218693863.9, dated Aug. 23, 2024.

Extended European Search Report for European Application No. 21869386.9, dated Jan. 23, 2025.

Extended European Search Report for European Application No. 25196032.4, dated Oct. 31, 2025.

* cited by examiner

*Primary Examiner* — Golam M Shameem

(74) *Attorney, Agent, or Firm* — Birch, Stewart, Kolasch & Birch, LLP

(57) ABSTRACT

The present invention provides a salt of a triazine compound which has an inhibitory action against aldosterone synthase and is useful as a drug, and especially as a drug for preventing or treating primary aldosteronism and the like, a crystal thereof, and a method for producing the same. Specifically, the present invention provides a pharmaceutically acceptable salt of 3-[4-[[trans-4-(acetamino)cyclohexyl]carbamoylmethyl]piperazin-1-yl]-5-(p-tolyl)-1,2,4-triazine, wherein the salt is hydrobromide, sulfate, succinate, or tosylate, and the like.

15 Claims, 11 Drawing Sheets

TRIAZINE COMPOUND SALT, CRYSTAL FORM THEREOF, AND PRODUCTION METHOD THEREFOR

CROSS-REFERENCE TO RELATED APPLICATIONS

This application is the National Phase of PCT International Application No. PCT/JP2021/033901, filed on Sep. 15, 2021, which claims priority under 35 U.S.C. § 119(a) to Patent Application No. 2020-154875, filed in Japan on Sep. 15, 2020, all of which are hereby expressly incorporated by reference into the present application.

TECHNICAL FIELD

The present invention relates to a salt of a triazine compound which has an inhibitory action against aldosterone synthase and is useful as a drug, and especially as a drug for preventing or treating primary aldosteronism and the like, a crystal form thereof, and a method for producing the same. More specifically, the present invention relates to 3-[4-[[trans-4-(acetamino)cyclohexyl]carbamoylmethyl]piperazin-1-yl]-5-(p-tolyl)-1,2,4-triazine (hereinafter also referred to as "Triazine compound A") or a pharmaceutically acceptable salt thereof having excellent physical properties as an active pharmaceutical ingredient, a crystal form thereof, a method for producing the same, a pharmaceutical composition comprising the same as an active ingredient, and the like.

BACKGROUND ART

Patent Document 1 discloses a plurality of triazine compounds or pharmacologically acceptable salts thereof having aldosterone synthase inhibitory activities, and Example 48 in said document discloses the Triazine compound A. However, Patent Document 1 neither discloses nor suggests a specific salt or crystal form of the Triazine compound A.

Also, Patent Document 1 discloses the following method for producing the Triazine compound A.

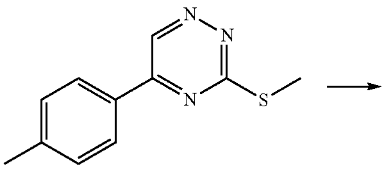

(B)

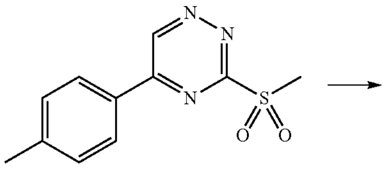

(C)

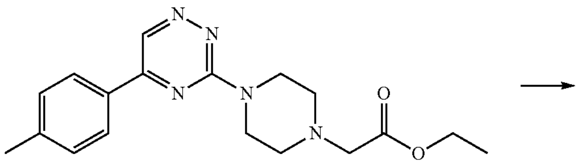

(D)

-continued

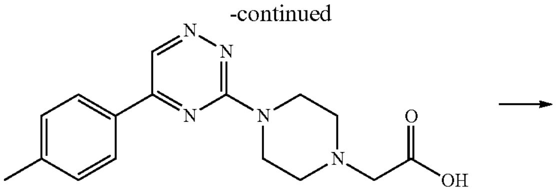

(E)

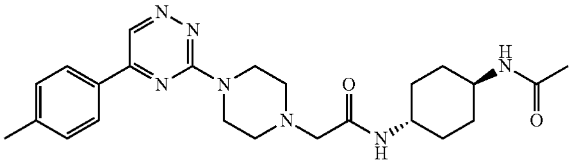

(A)

CITATION LIST

Patent Document

Patent Document 1: WO 2015/163427 pamphlet

SUMMARY OF THE INVENTION

Problems to be Solved by the Invention

The present invention provides novel salts of the Triazine compound A used in the prevention or treatment of primary aldosteronism and the like, crystal forms thereof, and an industrially advantageous method for producing said compound.

Means to Solve Problems

In order to solve the above problems, the present inventors have earnestly studied to obtain an active pharmaceutical ingredient having a specific level of quality suitable as a medicament, and they have tried to obtain a salt. As a result, hydrobromide, sulfate, succinate, or tosylate of the Triazine compound A have been found as salts that can produce excellent crystals that are excellent in terms of purity, thermal stability, hygroscopicity, deliquescency, chemical stability, and safety, as well as in terms of handling.

Next, the present inventors have earnestly studied the above salts of the Triazine compound A. As a result, they have found that hydrobromide of the Triazine compound A shows stable pharmacokinetics under both increased gastric acid secretion and reduced gastric acid secretion.

The hydrobromide of the Triazine compound A has unexpectedly excellent physical properties as an active pharmaceutical ingredient as stated above, and also has been proved to have various crystal forms. The present inventors have found that a Hydrobromide Form A crystal of the Triazine compound A is the most preferable crystal form among others in terms of stability and the like. However, problems such as incorporation of polymorph, increase of impurities, and increase of residual solvent(s) have been found depending on the amount of hydrogen bromide to be added in the crystallization step, crystallization temperature, and composition of crystallization solvent, and the target crystal could not be reproducibly stably produced. Thus, the present inventors have also earnestly studied the type, amount, and ratio of reagents and solvents to be used in crystallization, as well as the crystallization procedure and the like. As a result, they have found a method for efficiently producing the Hydrobromide Form A crystal of the Triazine compound A which is a crystal having appropriate qualities as an active pharmaceutical ingredient, and completed the present invention. Further, they have found a method for producing stable crystal forms having excellent qualities also from sulfate, succinate, and tosylate of the Triazine compound A like the Hydrobromide Form A crystal of the Triazine compound A.

Further, the production intermediate compounds disclosed in the Patent Document 1, i.e., the Compounds (B), (C), and (E), have been confirmed to have an explosive risk as a result of differential scanning calorimetry. Also, the Compounds (B), (C), and (D) have been confirmed to have a potential genotoxic risk as a result of genotoxic risk assessment by DEREK; MultiCASE. Namely, the production method disclosed in the Patent Document 1 uses compounds having an explosive risk and a genotoxic risk as production intermediate compounds, and thus a disadvantageous production method for carrying out in an industrial scale.

In addition, the Triazine compound A is a hardly soluble compound, has similar physical properties to insoluble impurities and the like produced in intermediate step(s), thus is not easy to carry out the purification such as isolation in the final step, and it has been difficult to obtain the Triazine compound A having appropriate qualities as an active pharmaceutical ingredient.

Thus, the present inventors have carried out various studies. As a result, they have found an industrially advantageous method for producing the Triazine compound A having appropriate qualities as an active pharmaceutical ingredient in which insoluble impurities can be easily removed by using compounds having a reduced explosive risk and a reduced genotoxic risk as production intermediate compounds, and using highly soluble compounds as production intermediate compounds.

Namely, the present invention provides the followings.

[1]

A pharmaceutically acceptable salt of 3-[4-[[trans-4-(acetamino)cyclohexyl]carbamoylmethyl]piperazin-1-yl]-5-(p-tolyl)-1,2,4-triazine, wherein the salt is hydrobromide, sulfate, succinate, or tosylate.

[2]

The salt according to [1], wherein the salt is hydrobromide.

[3]

A crystal of the salt according to [1].

[4]

The crystal according to [3], wherein the salt is hydrobromide.

[4-1]

The crystal according to [3], wherein the salt is dihydrobromide.

[4-2]

The crystal according to any one of [3] to [4-1], wherein the salt is hydrate.

[5]

The crystal according to any one of [4] to [4-2] having peaks at 8.8°±0.2°, 18.10°±0.2°, 20.9°±0.2°, and 25.6°±0.2° as diffraction angles expressed in 2θ in a powder X-ray diffraction spectrum.

[6]

The crystal according to any one of [4] to [5] having an endothermic peak at 265 to 275° C. in a differential scanning calorimetry analysis.

[7]

An aldosterone synthase inhibitor comprising the crystal according to any one of [3] to [6] as an active ingredient.

[8]

A pharmaceutical composition comprising the crystal according to any one of [3] to [6] and a pharmaceutically acceptable additive.

[9]

The pharmaceutical composition according to [8] for preventing or treating a disease of which a pathological condition is expected to be improved by the inhibition of aldosterone synthase.

[10]

The pharmaceutical composition according to [9], wherein the disease is one or more disease(s) selected from the group consisting of primary aldosteronism, secondary aldosteronism, hypertension, heart failure, cardiomyopathy, cardiac hypertrophy, myocardial infarction, myocardial necrosis lesion, disorder after myocardial ischemia, coronary artery disease, fibrosis or remodeling of myocardium or blood vessel, vascular restenosis, blood vessel wall thickening, arterial sclerosis, acute renal disorder, chronic kidney disease, renal fibrosis, nephropathy, hypokalemia, metabolic syndrome, obesity, sleep apnea syndrome, retinopathy, hepatic disease, idiopathic and/or cyclic edema, and sympathetic hyperactivity.

[11]

A method for preventing or treating a disease of which a pathological condition is expected to be improved by the inhibition of aldosterone synthase comprising administering an effective amount of the crystal according to any one of [3] to [6] to a patient.

[12]

Use of the crystal according to any one of [3] to [6] in the manufacture of a medicament for preventing or treating a disease of which a pathological condition is expected to be improved by the inhibition of aldosterone synthase.

[13]

The crystal according to any one of [3] to [6] for preventing or treating a disease of which a pathological condition is expected to be improved by the inhibition of aldosterone synthase.

[14]

A method for producing 3-[4-[[trans-4-(acetamino)cyclohexyl]carbamoylmethyl]piperazin-1-yl]-5-(p-tolyl)-1,2,4-triazine represented by a Compound (10), wherein the method is represented by the following reaction scheme:

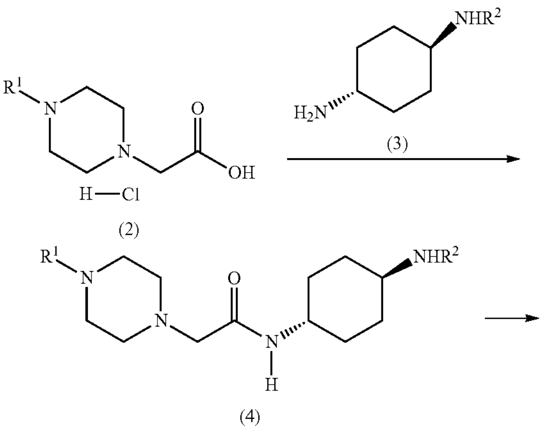

(2) (3) (4)

-continued

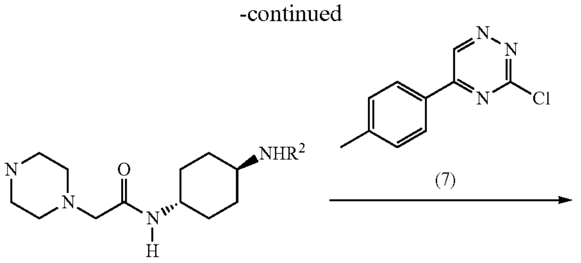
(7)

(5)

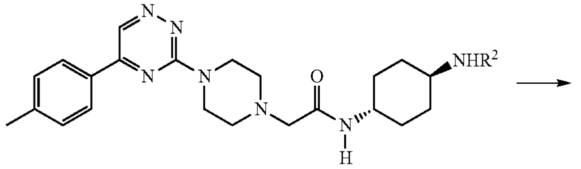

(8)

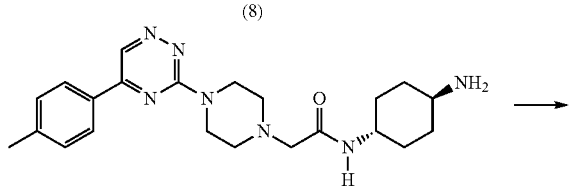

(9)

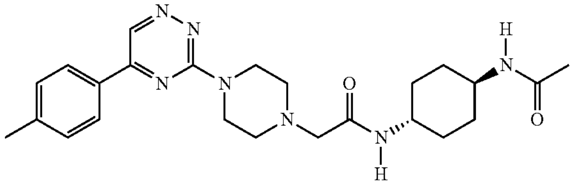

(10)

(wherein $R^1$ and $R^2$ each independently represent an amino protecting group)

and comprising the following steps:

(Step 1) a step of reacting the Compound (2) with the Compound (3) to produce the Compound (4) or a salt thereof;

(Step 2) a step of subjecting the Compound (4) or a salt thereof to a deprotection reaction to produce the Compound (5) or a salt thereof;

(Step 3) a step of reacting the Compound (5) or a salt thereof with the Compound (7) to produce the Compound (8) or a salt thereof;

(Step 4) a step of subjecting the Compound (8) or a salt thereof to a deprotection reaction to produce the Compound (9) or a salt thereof; and (Step 5) a step of reacting the Compound (9) or a salt thereof with an acetylating agent to produce the Compound (10).

[15]

A method for producing a crystal of 3-[4-[[trans-4-(acetamino)cyclohexyl]carbamoylmethyl]piperazin-1-yl]-5-(p-tolyl)-1,2,4-triazine hydrobromide characterized by adding 0.9 to 1.1 equivalent(s) of hydrogen bromide to 3-[4-[[trans-4-(acetamino)cyclohexyl]carbamoylmethyl]piperazin-1-yl]-5-(p-tolyl)-1,2,4-triazine in a mixed solvent of water and acetone having a water content of 2.0 to 3.0% by volume to produce said crystal.

[16]

A compound represented by formula (4)

(4)

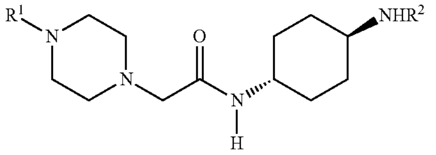

(wherein $R^1$ and $R^2$ each independently represent an amino protecting group)

or a salt thereof.

[17]

A compound represented by formula (5)

(5)

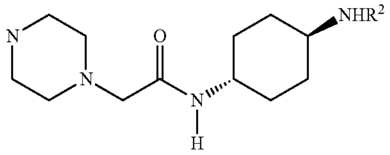

(wherein $R^2$ represents an amino protecting group) or a salt thereof.

[18]

A compound represented by formula (8)

(8)

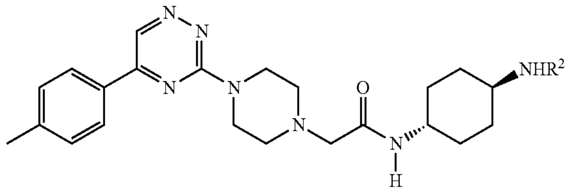

(wherein $R^2$ represents an amino protecting group) or a salt thereof.

Effect of Invention

Hydrobromide, sulfate, succinate, and tosylate of the Triazine compound A of the present invention are excellent salts as active pharmaceutical ingredients. Especially, crystals thereof comprise no residual solvent, have excellent thermal stability, are stable under humid conditions with reduced weight change, not deliquescent, and have excellent chemical stability. Thus, salts of the Triazine compound A or crystals thereof are useful as active pharmaceutical ingredients.

In particular, hydrobromide of the Triazine compound A of the present invention shows stable pharmacokinetics under both increased gastric acid secretion and reduced gastric acid secretion. Also, crystals thereof have excellent stability and purity, and the present invention has established a method for stably producing them as crystals comprising no compound that may have adverse effects on living bodies in terms of safety. Accordingly, hydrobromide of the Triazine compound A or crystals thereof are especially useful as active pharmaceutical ingredients.

In addition, the method for producing the Triazine compound A of the present invention can reproducibly produce the Triazine compound A by an industrially appropriate method, and thus is useful as an industrial method for producing active pharmaceutical ingredients having excellent qualities.

MODE FOR CARRYING OUT THE INVENTION

Figure 1:
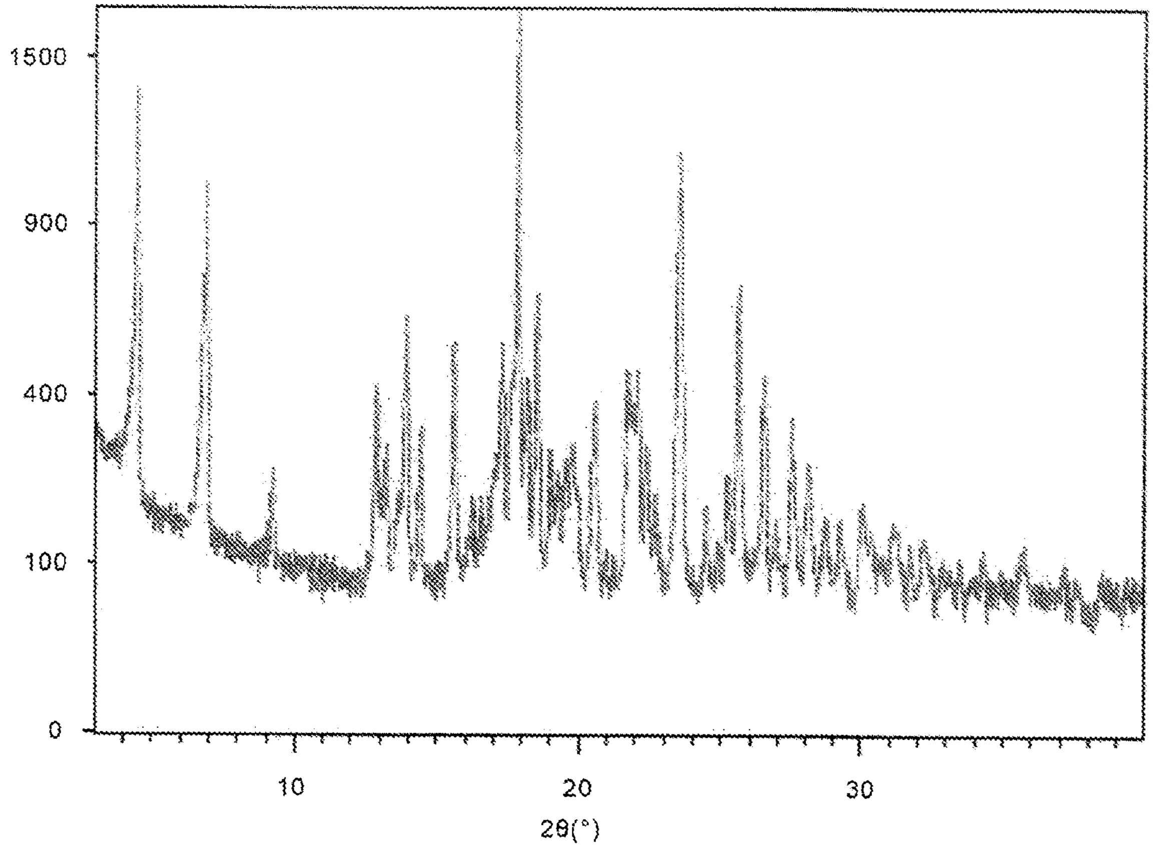
FIG. 1 is a figure showing a result of a powder X-ray diffraction measurement of Sulfate Form B crystals of the Triazine compound A.
Figure 2:
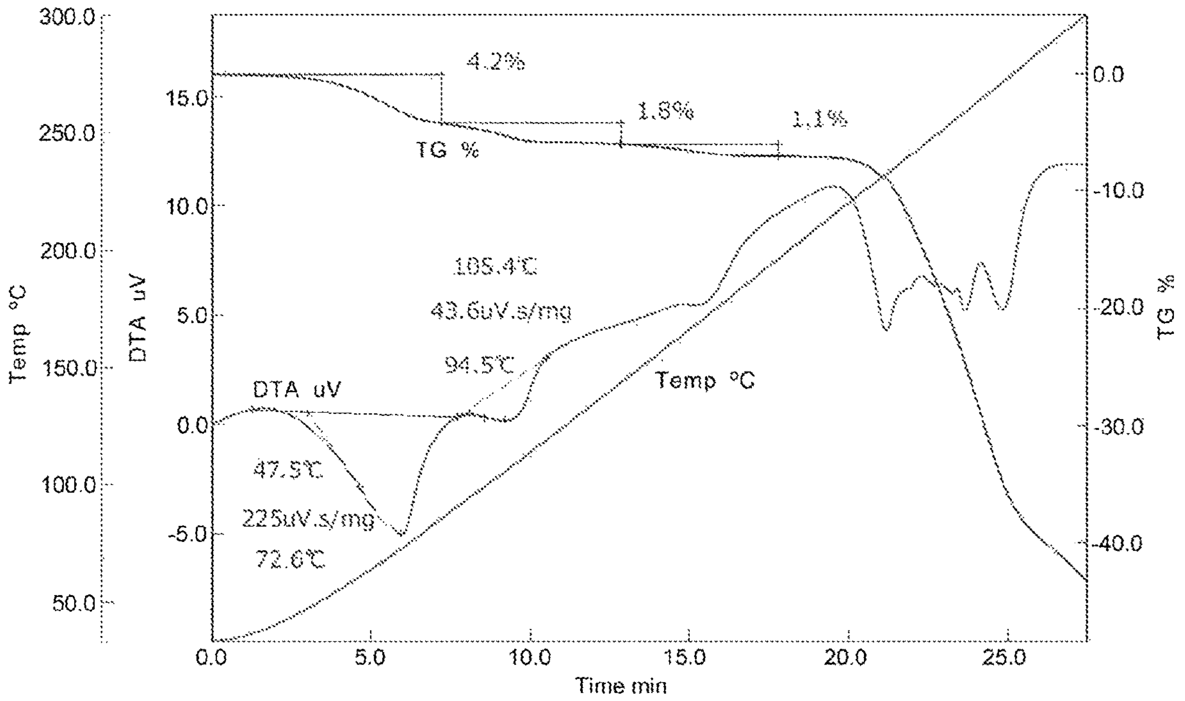
FIG. 2 is a figure showing a result of differential scanning calorimetry of Sulfate Form B crystals of the Triazine compound A.
Figure 3:
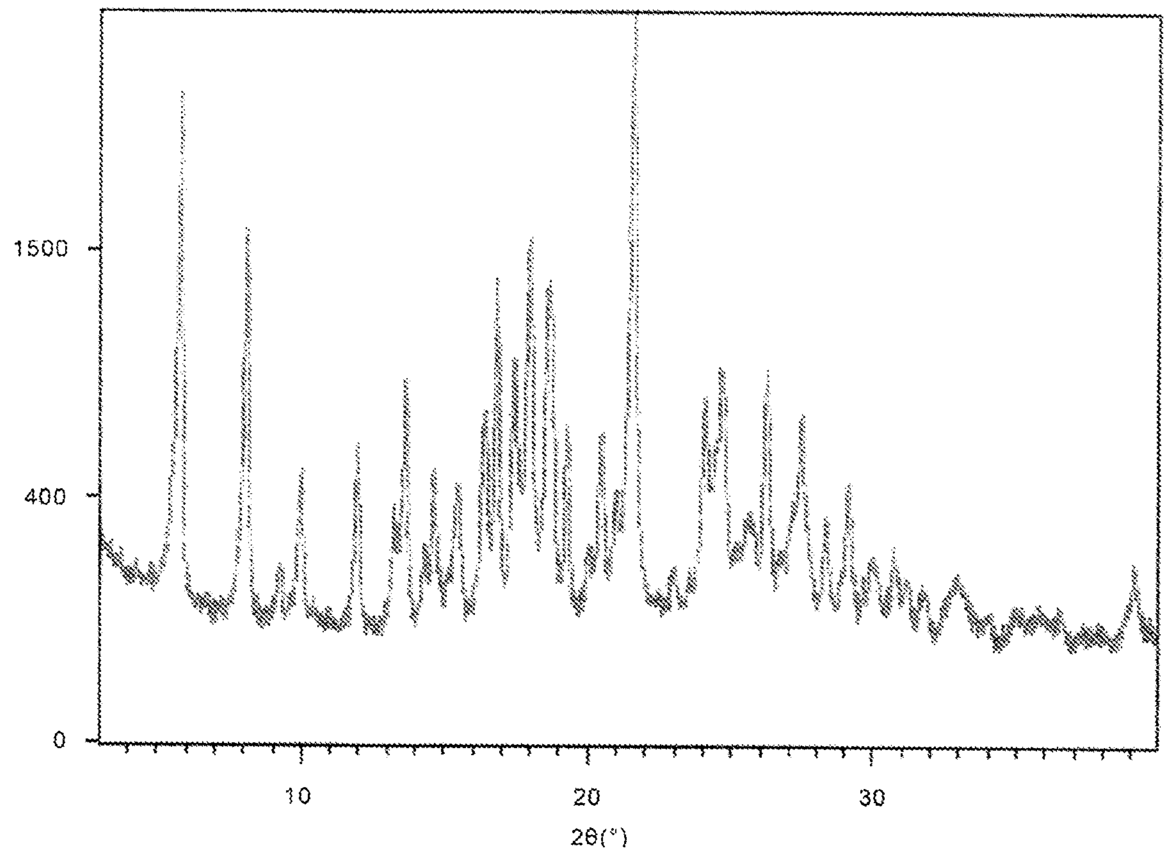
FIG. 3 is a figure showing a result of a powder X-ray diffraction measurement of Tosylate Form C crystals of the Triazine compound A.
Figure 4:
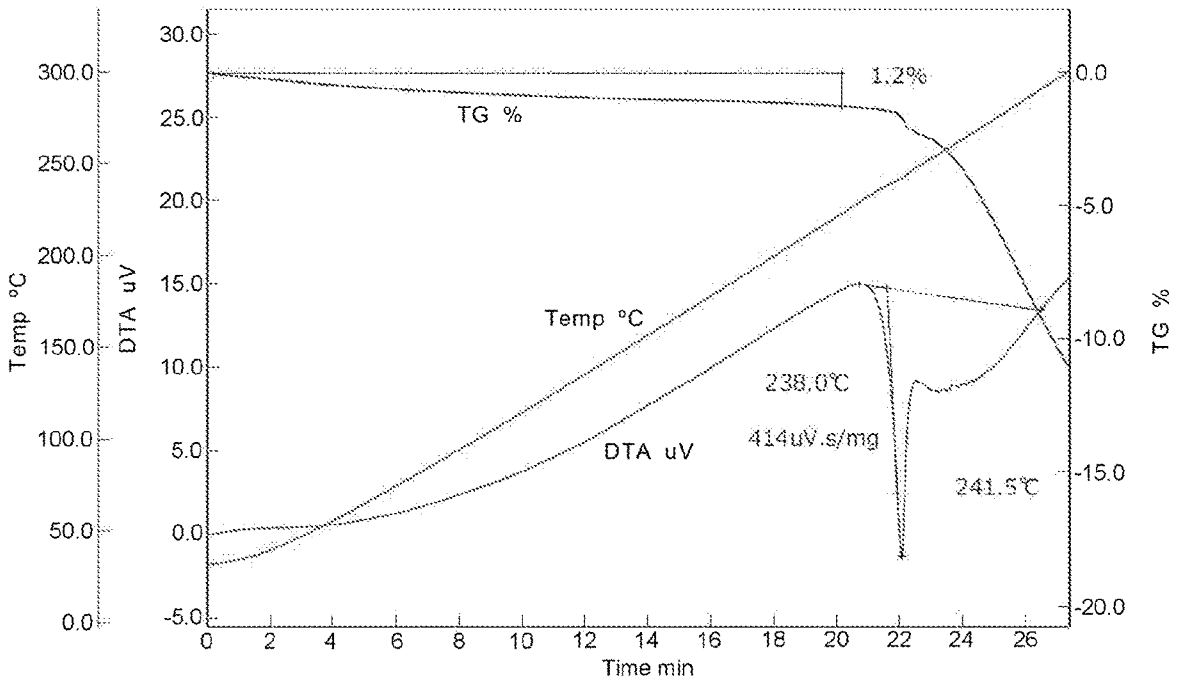
FIG. 4 is a figure showing a result of differential scanning calorimetry of Tosylate Form C crystals of the Triazine compound A.
Figure 5:
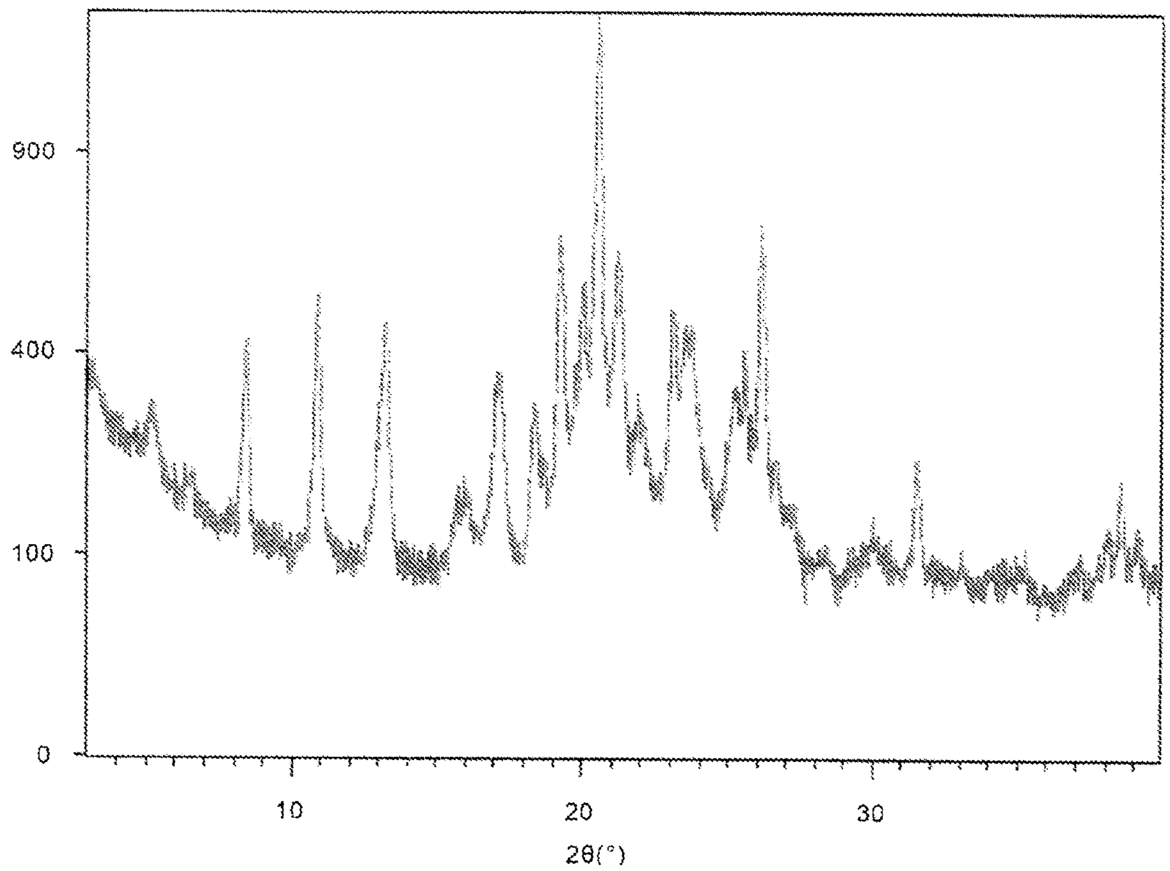
FIG. 5 is a figure showing a result of a powder X-ray diffraction measurement of Succinate Form A crystals of the Triazine compound A.
Figure 6:
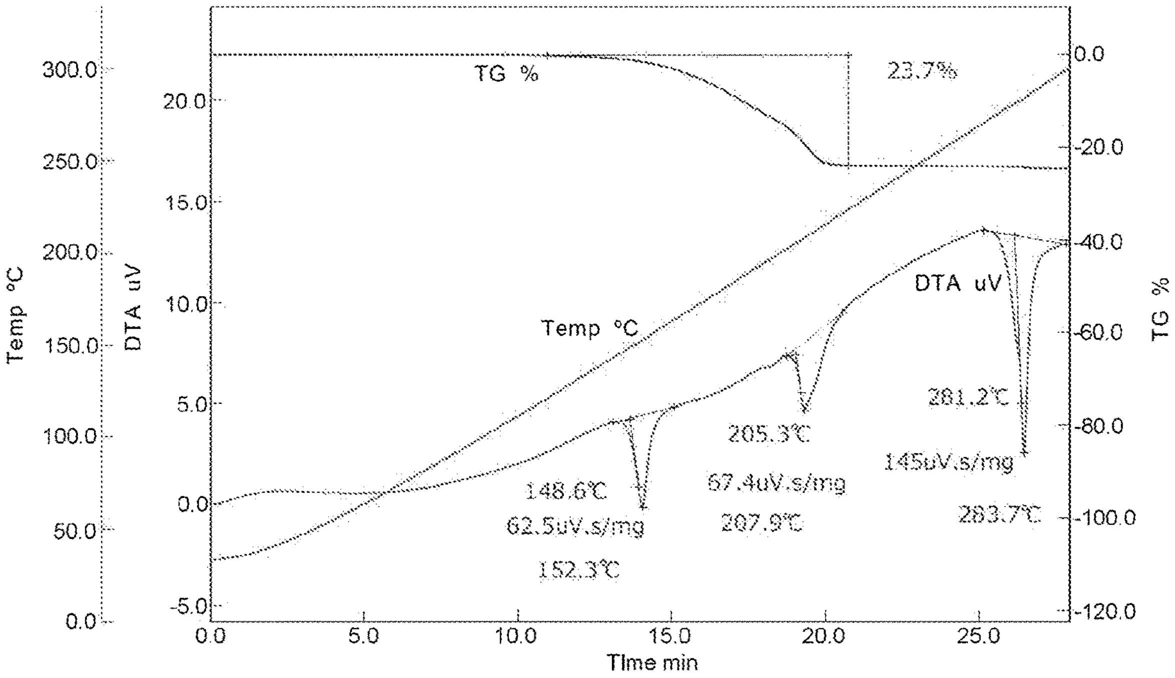
FIG. 6 is a figure showing a result of differential scanning calorimetry of Succinate Form A crystals of the Triazine compound A.

In the present description, each substituent represented by each symbol has the following meaning.

The term of "amino protecting group" means a protecting group usually used in the field of synthetic organic chemistry, and examples thereof include a t-butoxycarbonyl group, a benzyloxycarbonyl group, and a p-methoxybenzyl group. Among them, a t-butoxycarbonyl group and a benzyloxycarbonyl group are preferable.

The Triazine compound A may be produced according to the following scheme.

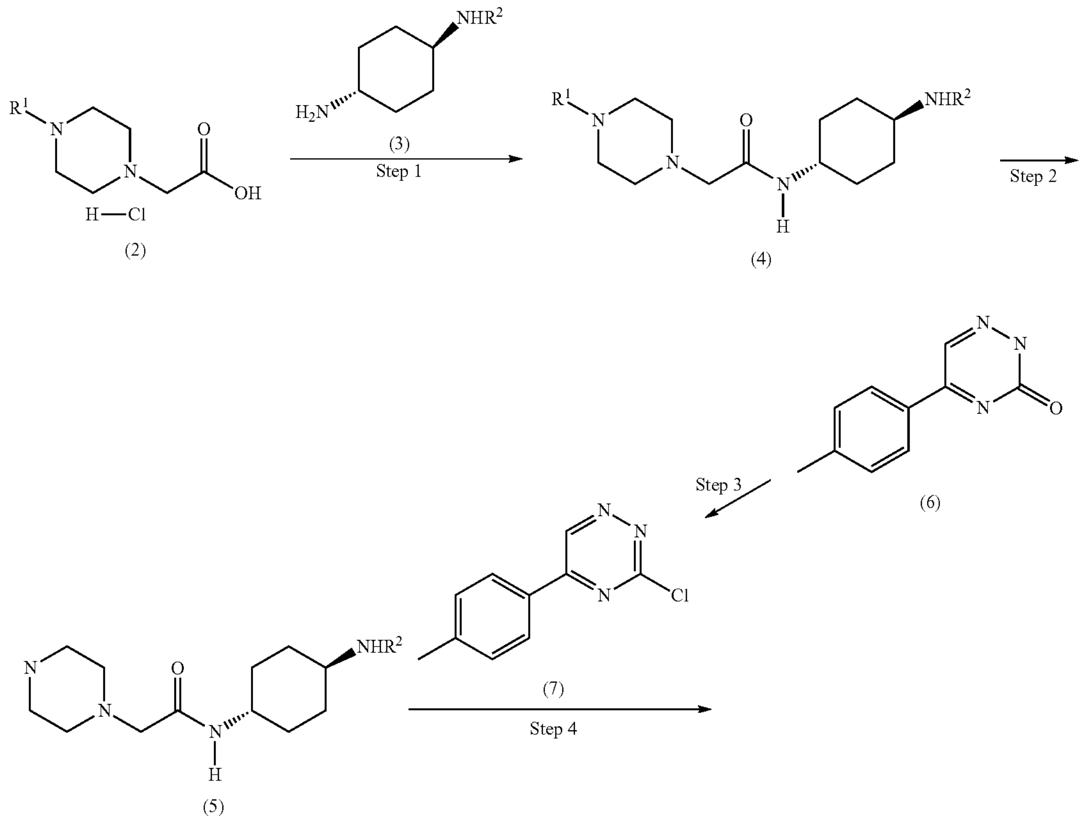

(2) (4) (6) (5)

-continued

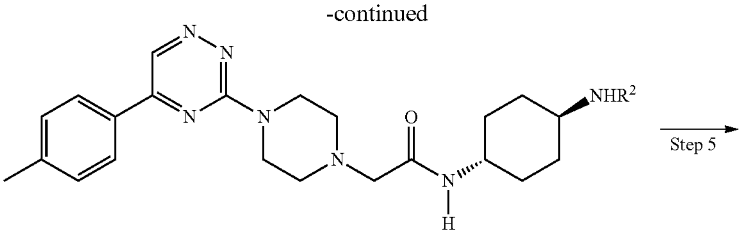

(8)

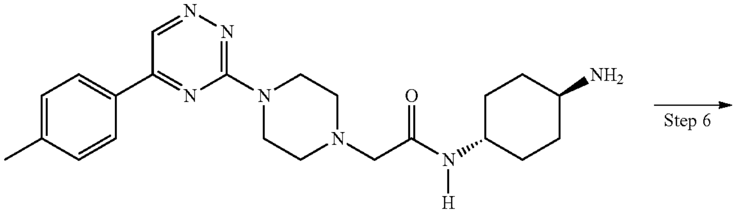

(9)

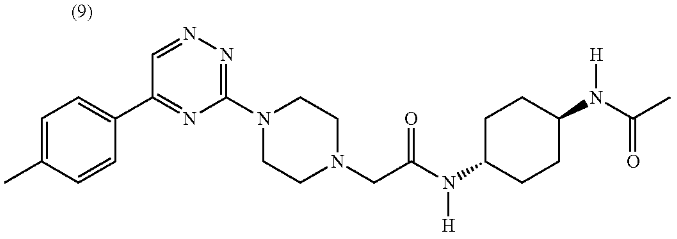

(10)

(wherein $R^1$ represents an amino protecting group such as a benzyloxycarbonyl group, and $R^2$ represents an amino protecting group such as a t-butoxycarbonyl group and a different amino protecting group from $R^1$)

Step 1:

Step 1 is a step of reacting the Compound (2) with the Compound (3) to produce the Compound (4) or a salt thereof. The Compound (2) and the Compound (3) are known, or may be produced according to known method(s). Examples of the salt of the Compound (4) include acid addition salts, and specific examples thereof include inorganic acid salts such as hydrochloride, sulfate, phosphate, and hydrobromide, and organic acid salts such as acetate, fumarate, oxalate, citrate, methanesulfonate, benzenesulfonate, tosylate, and maleate. Preferable examples thereof include hydrochloride.

The reaction of the Compound (2) with the Compound (3) may be carried out according to method(s) disclosed in WO 2015/163427 pamphlet or the like, and may be carried out by, for example, reacting the Compound (2), the Compound (3), and a condensing agent in a solvent in the presence of a base.

Examples of the condensing agent include carbodiimides, acid azides, phosphonium condensing agents, triazoles, and acid anhydrides, and preferable examples thereof include acid anhydrides, and especially preferable examples thereof include propanephosphonic acid anhydride.

The solvent is not limited as long as it does not affect the present reaction, and examples thereof include aromatic hydrocarbons (for example, benzene, toluene, and xylene), aprotic solvents (for example, N,N-dimethylformamide, N,N-dimethylacetamide, dimethylsulfoxide, and N-methyl-2-pyrrolidone), nitriles (for example, acetonitrile), ketones (for example, acetone and methyl ethyl ketone), esters (for example, ethyl acetate), and ethers (for example, diethyl ether, tetrahydrofuran, and dimethoxyethane), and they may also be used in an appropriate combination with each other. Among them, nitriles are preferable, and especially acetonitrile is preferable.

Examples of the base include triethylamine, diisopropylethylamine, and 1,8-diazabicyclo[5.4.0]undec-7-ene (DBU), and among them, diisopropylethylamine is preferable.

The amount of the Compound (3) to be used is 1.0 to 1.5 equivalent(s), and preferably 1.0 to 1.1 equivalent(s), relative to the Compound (2). The amount of the condensing agent to be used is 0.9 to 1.5 equivalent(s), and preferably 1.0 to 1.2 equivalent(s), relative to the Compound (2). The amount of the base to be used is 1.0 to 1.5 equivalent(s), and preferably 1.0 to 1.3 equivalent(s), relative to the Compound (2). The present reaction may be carried out at 0 to 30° C.

Step 2:

Step 2 is a step of subjecting the Compound (4) or a salt thereof to a deprotection reaction to produce the Compound (5) or a salt thereof. Examples of the salt of the Compound (5) include acid addition salts, and specific examples thereof include inorganic acid salts such as hydrochloride, sulfate, phosphate, and hydrobromide, and organic acid salts such as acetate, fumarate, oxalate, citrate, methanesulfonate, benzenesulfonate, tosylate, and maleate. Preferable examples thereof include hydrochloride.

The deprotection reaction of the Compound (4) may be carried out according to the method(s) disclosed in Theodora W. Greene, Peter G. M. Wuts, "Protective Groups in Organic Synthesis" 4th. Ed./John Wiley & Sons, Inc., 2007 or the like, and for example, in a solvent, in the presence of palladium carbon, and under hydrogen atmosphere.

The solvent is not limited as long as it does not affect the present reaction, and examples thereof include aprotic solvents (for example, N,N-dimethylformamide, N,N-dimethylacetamide, dimethylsulfoxide, and N-methyl-2-pyrrolidone), nitriles (for example, acetonitrile), ketones (for example, acetone and methyl ethyl ketone), esters (for example, ethyl acetate), ethers (for example, diethyl ether, tetrahydrofuran, and dimethoxyethane), and alcohols (for example, methanol, ethanol, and isopropanol), and they may also be used in an appropriate combination with each other. Among them, alcohols are preferable, and methanol is more preferable.

The amount of palladium carbon to be used is 0.1 to 10% by weight, and preferably 0.5 to 10% by weight, relative to the Compound (4) or a salt thereof. The present reaction may be carried out at 0 to 30° C.

Step 3:

Step 3 is a step of chlorinating the Compound (6) to produce the Compound (7). The Compound (6) is known, or may be produced according to known method(s). The chlorinating reaction of the Compound (6) may be carried out in a solvent in the presence of a chlorinating agent. The reaction may also be carried out in the presence of a catalyst as needed.

The solvent is not limited as long as it does not affect the present reaction, and examples thereof include aromatic hydrocarbons (for example, benzene, toluene, and xylene), aprotic solvents (for example, N,N-dimethylformamide, N,N-dimethylacetamide, dimethylsulfoxide, and N-methyl-2-pyrrolidone), nitriles (for example, acetonitrile), ketones (for example, acetone and methyl ethyl ketone), esters (for example, ethyl acetate), and ethers (for example, diethyl ether, tetrahydrofuran, and dimethoxyethane), and they may also be used in an appropriate combination with each other. Among them, ethers are preferable, and dimethoxyethane is more preferable.

Examples of the chlorinating agent include thionyl chloride, phosphorus oxychloride, and oxalyl chloride, and among them, thionyl chloride is preferable.

The amount of the chlorinating agent to be used is 1.0 to 3.0 equivalent(s), and preferably 1.8 to 2.2 equivalents, relative to the Compound (6).

Preferable examples of the catalyst include N,N-dimethylformamide.

The amount of the catalyst to be used is 0.01 to 0.5 equivalent, and preferably 0.05 to 0.1 equivalent, relative to the Compound (6).

The present reaction may be carried out at 50 to 100° C., and preferably at 70 to 80° C.

Step 4:

Step 4 is a step of reacting the Compound (5) or a salt thereof with the Compound (7) to produce the Compound (8) or a salt thereof. Examples of the salt of the Compound (8) include acid addition salts, and specific examples thereof include inorganic acid salts such as hydrochloride, sulfate, phosphate, and hydrobromide, and organic acid salts such as acetate, fumarate, oxalate, citrate, methanesulfonate, benzenesulfonate, tosylate, and maleate. Preferable examples thereof include hydrochloride.

The present reaction may be carried out in a solvent in the presence of a base.

The solvent is not limited as long as it does not affect the present reaction, and examples thereof include aprotic solvents (for example, N,N-dimethylformamide, N,N-dimethylacetamide, dimethylsulfoxide, and N-methyl-2-pyrrolidone), nitriles (for example, acetonitrile), ketones (for example, acetone and methyl ethyl ketone), esters (for example, ethyl acetate), ethers (for example, diethyl ether, tetrahydrofuran, and dimethoxyethane), and alcohols (for example, methanol, ethanol, and isopropanol), and they may also be used in an appropriate combination with each other. Among them, aprotic solvents and alcohols are preferable, N-methyl-2-pyrrolidone and methanol are more preferable, and a mixed solvent of N-methyl-2-pyrrolidone and methanol is still more preferable.

Examples of the base include triethylamine, diisopropylethylamine, and 1,8-diazabicyclo[5.4.0]undec-7-ene (DBU), and among them, triethylamine is preferable.

The amount of the base to be used is 1 to 5 equivalent(s), and preferably 2 to 3 equivalents, relative to the Compound (7). The present reaction may be carried out at 50 to 100° C., and preferably 50 to 70° C.

Step 5:

Step 5 is a step of subjecting the Compound (8) or a salt thereof to a deprotection reaction to produce the Compound (9) or a salt thereof. Examples of the salt of the Compound (9) include acid addition salts, and specific examples thereof include inorganic acid salts such as hydrochloride, sulfate, phosphate, and hydrobromide, and organic acid salts such as acetate, fumarate, oxalate, citrate, methanesulfonate, benzenesulfonate, tosylate, and maleate. Preferable examples thereof include hydrochloride.

The deprotection reaction of the Compound (8) may be carried out according to the method(s) disclosed in Theodora W. Greene, Peter G. M. Wuts, "Protective Groups in Organic Synthesis" 4th. Ed./John Wiley & Sons, Inc., 2007 or the like. For example, the present reaction may be carried out in a solvent in the presence of an acid.

The solvent is not limited as long as it does not affect the present reaction, and examples thereof include water, aprotic solvents (for example, N,N-dimethylformamide, N,N-dimethylacetamide, dimethylsulfoxide, and N-methyl-2-pyrrolidone), nitriles (for example, acetonitrile), ketones (for example, acetone and methyl ethyl ketone), esters (for example, ethyl acetate), ethers (for example, diethyl ether, tetrahydrofuran, and dimethoxyethane), and alcohols (for example, methanol, ethanol, and isopropanol), and they may also be used in an appropriate combination with each other. Among them, water is preferable.

Examples of the acid include trifluoroacetic acid, hydrochloric acid, p-toluenesulfonic acid, and methanesulfonic acid, and among them, hydrochloric acid is preferable.

The amount of the acid to be used is 3 to 10 equivalents, and preferably 3 to 5 equivalents, relative to the Compound (8). The present reaction may be carried out at 30 to 50° C.

The mixture comprising the resulting Compound (9) or a salt thereof after the reaction may be directly used in the next step, but it is preferable to use said mixture in the next step after insoluble matters are removed. When the insoluble matters are removed, it is more preferable to filter the mixture. When the mixture is filtered, it is preferable to use the same solvent as that used in the reaction. The temperature at the filtration is preferably 5 to 95° C., and more preferably 30 to 50° C. It is more preferable to carry out crystallization from the filtrate to obtain the Compound (9) as solids, and then use them in the next step.

Step 6:

Step 6 is a step of reacting the Compound (9) or a salt thereof with an acetylating agent to produce the Compound (10). The reaction of the Compound (9) or a salt thereof with an acetylating agent may be carried out in a solvent.

The solvent is not limited as long as it does not affect the present reaction, and examples thereof include aromatic hydrocarbons (for example, benzene, toluene, and xylene), aprotic solvents (for example, N,N-dimethylformamide, N,N-dimethylacetamide, dimethylsulfoxide, and N-methyl-2-pyrrolidone), nitriles (for example, acetonitrile), ketones (for example, acetone and methyl ethyl ketone), esters (for example, ethyl acetate), ethers (for example, diethyl ether, tetrahydrofuran, and dimethoxyethane), and alcohols (for example, methanol, ethanol, and isopropanol), and they may also be used in an appropriate combination with each other. Among them, aromatic hydrocarbons and alcohols are preferable, toluene and methanol are more preferable, and a mixed solvent of toluene and methanol is still more preferable.

Examples of the acetylating agent include acetyl chloride and acetic anhydride, and among them, acetic anhydride is preferable.

The amount of the acetylating agent to be used is 1 to 1.5 equivalent(s), and preferably 1.05 to 1.2 equivalents, relative to the Compound (9) or a salt thereof. The present reaction may be carried out at 40 to 60° C.

The Compound (4), the Compound (5), and the Compound (8) are novel production intermediate compounds for producing the Compound (10).

The present invention relates to salts of the Triazine compound A, crystals thereof, and a method for producing the same.

The salts of the present invention are salts of the Triazine compound A, preferably hydrobromide, sulfate, tosylate, and succinate of the Triazine compound A, and more preferably hydrobromide of the Triazine compound A.

The molar ratio of the acid relative to the Triazine compound A is not specifically limited. For example, the molar ratio of the acid relative to the Triazine compound A may be 1 to 3 equivalent (s). For example, hydrobromide of the Triazine compound A includes monohydrobromide of the Triazine compound A, dihydrobromide of the Triazine compound A, and the like.

Also, the salt of the Triazine compound A may be hydrate.

The crystals of the present invention are crystals of salts of the Triazine compound A, preferably a crystal of hydrobromide of the Triazine compound A, a crystal of sulfate of the Triazine compound A, a crystal of tosylate of the Triazine compound A, and a crystal of succinate of the Triazine compound A, more preferably a crystal of hydrobromide of the Triazine compound A, and still more preferably Hydrobromide Form A crystal of the Triazine compound A.

The crystal of sulfate of the Triazine compound A is preferably a Sulfate Form B crystal of the Triazine compound A.

The crystal of tosylate of the Triazine compound A is preferably a Tosylate Form C crystal of the Triazine compound A.

The crystal of succinate of the Triazine compound A is preferably a Succinate Form A crystal of the Triazine compound A.

A method for producing a crystal of hydrobromide of the Triazine compound A is described below. The crystal of hydrobromide of the Triazine compound A has a plurality of crystal forms, and especially preferable crystal forms are Form A, Form F, and Form N crystals. Among them, the Form A crystal is more especially preferable. However, the simple addition of hydrogen bromide to Triazine compound A in a solvent also produces Form F crystals and Form N crystals. In this regard, the appropriate control of the amount of hydrogen bromide to be added, the amount of water present in the reaction system, the crystallization temperature, and the like makes the crystal forms to converge on Form A crystals, to stably and efficiently produce Form A crystals only.

The Hydrobromide Form A crystal of the Triazine compound A may be produced as follows.

The Compound (10) is reacted with 0.9 to 1.1 equivalent(s) of hydrogen bromide, preferably 0.95 to 1.05 equivalent(s) of hydrogen bromide, and the resulting mixture is subjected to crystallization to produce Hydrobromide Form A crystals of the Triazine compound A. Said reaction may be carried out in a solvent.

Examples of the solvent include water, ketones (for example, acetone and methyl ethyl ketone), and alcohols (for example, methanol, ethanol, and isopropanol), and two or more kinds of solvents may also be used in an appropriate combination with each other. Preferable examples thereof include a mixed solvent of water and a water-miscible solvent. More preferable examples thereof include a mixed solvent having a water content of 1.0 to 5.0% relative to whole solvent volume. Especially, a mixed solvent of water and acetone having a water content of 1.0 to 5.0% relative to whole solvent volume in the reaction system is preferable, and a mixed solvent of water and acetone having a water content of 2.0 to 3.0% relative to whole solvent volume is more preferable.

The present reaction may be carried out at 5 to 55° C., preferably at 20 to 55° C., and more preferably at 40 to 55° C.

The Hydrobromide Form F crystal of the Triazine compound A may be produced as follows.

The Compound (10) is reacted with 2.0 to 2.2 equivalents of hydrogen bromide, and the resulting mixture is subjected to crystallization to produce Hydrobromide Form F crystals of the Triazine compound A. Said reaction may be carried out in a solvent.

Examples of the solvent include water, ketones (for example, acetone and methyl ethyl ketone), and alcohols (for example, methanol, ethanol, and isopropanol), and two or more kinds of solvents may also be used in an appropriate combination. Preferable examples thereof include a mixed solvent of water and acetone.

The present reaction may be carried out at 10 to 50° C., and preferably at 40 to 50° C.

The Hydrobromide Form N crystal of the Triazine compound A may be produced as follows.

The Compound (10) is reacted with 1.2 to 1.5 equivalents of hydrogen bromide, and the resulting mixture is subjected to crystallization to produce Hydrobromide Form N crystals of the Triazine compound A. Said reaction may be carried out in a solvent.

Examples of the solvent include water, ketones (for example, acetone and methyl ethyl ketone), and alcohols (for example, methanol, ethanol, and isopropanol), and two or more kinds of solvents may also be used in an appropriate combination with each other. Preferable examples thereof include water.

The present reaction may be carried out at 10 to 50° C., and preferably at 40 to 50° C.

The crystal of sulfate of the Triazine compound A may be produced as follows.

The Compound (10) is reacted with sulfuric acid, and the resulting mixture is subjected to crystallization to produce crystals of sulfate of the Compound (10). Said reaction may be carried out in a solvent.

The solvent is not limited as long as it does not affect the present reaction, and examples thereof include water, aprotic solvents (for example, N,N-dimethylformamide, N,N-dimethylacetamide, dimethylsulfoxide, and N-methyl-2-pyrrolidone), nitriles (for example, acetonitrile), ketones (for example, acetone and methyl ethyl ketone), esters (for example, ethyl acetate), ethers (for example, diethyl ether, tetrahydrofuran, and dimethoxyethane), alcohols (for example, methanol, ethanol, and isopropanol), and aromatic hydrocarbons (for example, benzene, toluene, and xylene), and they may also be used in an appropriate combination with each other.

The amount of sulfuric acid to be used is 1 to 10 equivalent(s), and preferably 1 to 5 equivalent(s), relative to the Compound (10). The present reaction may be carried out at 10 to 60° C.

The crystal of tosylate of the Triazine compound A may be produced as follows.

The Compound (10) is reacted with tosic acid, and the resulting mixture is subjected to crystallization to produce crystals of tosylate of the Compound (10). Said reaction may be carried out in a solvent.

The solvent is not limited as long as it does not affect the present reaction, and examples thereof include water, aprotic solvents (for example, N,N-dimethylformamide, N,N-dimethylacetamide, dimethylsulfoxide, and N-methyl-2-pyrrolidone), nitriles (for example, acetonitrile), ketones (for example, acetone and methyl ethyl ketone), esters (for example, ethyl acetate), ethers (for example, diethyl ether, tetrahydrofuran, and dimethoxyethane), alcohols (for example, methanol, ethanol, and isopropanol), and aromatic hydrocarbons (for example, benzene, toluene, and xylene), and they may also be used in an appropriate combination with each other.

The amount of tosic acid to be used is 1 to 10 equivalent (s), and preferably 1 to 5 equivalent(s), relative to the Compound (10). The present reaction may be carried out at 10 to 60° C.

The crystal of succinate of the Triazine compound A may be produced as follows.

The Compound (10) is reacted with succinic acid, and the resulting mixture is subjected to crystallization to produce crystals of succinate of the Compound (10). Said reaction may be carried out in a solvent.

The solvent is not limited as long as it does not affect the present reaction, and examples thereof include water, aprotic solvents (for example, N,N-dimethylformamide, N,N-dimethylacetamide, dimethylsulfoxide, and N-methyl-2-pyrrolidone), nitriles (for example, acetonitrile), ketones (for example, acetone and methyl ethyl ketone), esters (for example, ethyl acetate), ethers (for example, diethyl ether, tetrahydrofuran, and dimethoxyethane), alcohols (for example, methanol, ethanol, and isopropanol), and aromatic hydrocarbons (for example, benzene, toluene, and xylene), and they may also be used in an appropriate combination with each other.

The amount of succinic acid to be used is 1 to 10 equivalent(s), and preferably 1 to 5 equivalent(s), relative to the Compound (10). The present reaction may be carried out at 10 to 60° C.

The Triazine compound A and/or hydrogen bromide, sulfuric acid, tosic acid, and succinic acid in the crystal of the present invention encompass(es) compounds labeled with isotopes (for example, $^{3}H$, $^{13}C$, $^{14}C$, $^{15}N$, $^{18}F$, and $^{32}P$) or the like, and deuterated products.

In the crystal of the present invention, the Hydrobromide Form A crystal of the Triazine compound A does not comprise other residual molecules used in producing the crystal, and comprises the Triazine compound A and hydrogen bromide at a molar ratio of 1:1.

The Hydrobromide Form A crystal of the Triazine compound A is characterized by one or more of the followings.

Figure 11:
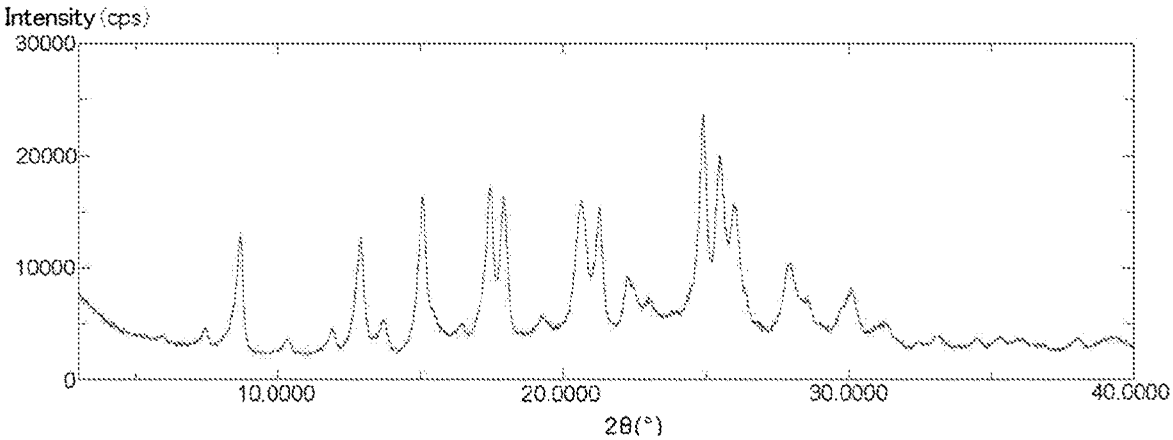
FIG. 11 is a figure showing a result of a powder X-ray diffraction measurement of Hydrobromide Form A crystals of the Triazine compound A.
Figure 12:
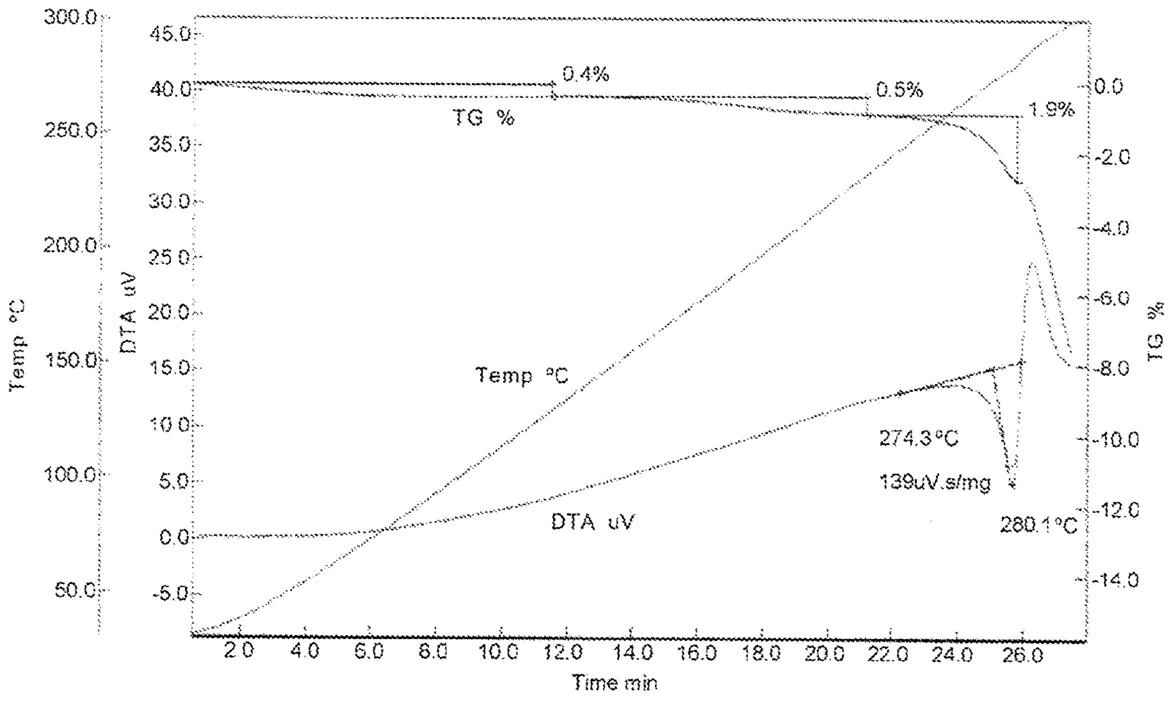
FIG. 12 is a figure showing a result of differential scanning calorimetry of Hydrobromide Form A crystals of the Triazine compound A.

(1) It preferably has a powder X-ray diffraction pattern indicated in FIG. 11 and/or a differential scanning calorimetry (DSC) curve indicated in FIG. 12.

(2) Characteristic peaks in a powder X-ray diffraction pattern of the Form A crystals include 8.8°±0.2° and 25.6°±0.2° as diffraction angles expressed in 2θ. In one embodiment, the Form A crystals have additional peaks at 18.1°±0.2° and 20.9°±0.2° as diffraction angles expressed in 2θ in a powder X-ray diffraction pattern. Other characteristic peaks thereof include 15.1°±0.2°, 17.5°±0.2°, 21.5°±0.2°, and 25.0°±0.2°. Still other characteristic peaks thereof include 13.0°±0.2°, 13.1°±0.2°, 13.8°±0.2°, 15.4°±0.2°, 19.6°±0.2°, 22.9°±0.2°, 26.2°±0.2°, 26.3°±0.2°, and 28.2°±0.2°. The Hydrobromide Form A crystal of the Triazine compound A is a crystal having substantially the same powder X-ray diffraction pattern as FIG. 11.

(3) The melting point measured by DSC (extrapolated onset temperature) is 265 to 275° C., and especially about 268° C.

The crystal of the present invention has an advantageous effect in that the amount of residual solvent(s) is below the standard value determined by the International Council for Harmonisation of Technical Requirements for Pharmaceuticals for Human Use (hereinafter referred to as "ICH"). Also, other effects include that the amounts of solvent impurities, inorganic impurities, residual metals, residual solvents, genotoxic impurities, and the like are below the standard values determined in the guideline of ICH.

The salts of the present invention and the crystals of the present invention have inhibitory actions against aldosterone synthase, and thus may be used as active ingredients of aldosterone synthase inhibitors, and the crystals of the present invention and pharmaceutical compositions comprising the same as active ingredients are useful for the treatment or prevention of various diseases of which pathological conditions are expected to be improved by the inhibition of aldosterone synthase. Examples of such diseases include primary aldosteronism (for example, unilateral or bilateral adrenal adenomas, unilateral or bilateral adrenal hyperplasia, aldosterone-producing adrenal carcinoma, unilateral adrenal multiple nodules aldosteronism, glucocorticoid reactive aldosteronism, familial aldosteronism, and ectopic aldosterone-producing tumors), secondary aldosteronism (for example, hypertension caused by an estrogen preparation, renal vascular hypertension, pregnancy hypertension, malignant hypertension, pheochromocytoma, congestive heart failure, pseudohypoaldosteronism, chronic liver disease associated with ascites (for example, hepatic cirrhosis), inappropriate use of a medicament such as a laxative and a diuretic, and hyperaldosteronemia associated with nephrotic syndrome, Bartter's syndrome, or Gitelman's syndrome), hypertension (for example, essential hypertension, secondary hypertension (for example, renal vascular hypertension, renal parenchymal hypertension, primary aldosteronism, pheochromocytoma, sleep apnea syndrome, Cushing's syndrome, drug induced hypertension, aortostenosis, and hyperparathyroidism), treatment-resistant hypertension, and mineralocorticoid-related hypertension), heart failure (for example, congestive heart failure, left ventricular failure, right ventricular failure, systolic dysfunction, and diastolic dysfunction), cardiomyopathy, cardiac hypertrophy (for example, left ventricular hypertrophy), myocardial infarction, myocardial necrosis lesion, disorder after myocardial ischemia, coronary artery disease, fibrosis or remodeling of myocardium or blood vessel (for example, cardiovascular fibrosis and remodeling caused by hypertension and/or vascular endothelial function disorder), vascular restenosis, blood vessel wall thickening, arterial sclerosis, renal failure (for example, chronic renal failure), acute renal disorder, chronic kidney disease, renal fibrosis, nephropathy (for example, diabetic nephropathy), hypokalemia, obesity, metabolic syndrome, sleep apnea syndrome, retinopathy (for example, diabetic retinopathy), hepatic disease, abnormal lipid metabolism, sympathetic hyperactivity, idiopathic and/or cyclic edema, headache, anxiety, and depressive disorder. In particular, a crystal of hydrobromide of the Triazine compound A is useful for the treatment or prevention of one or more disease(s) selected from the group consisting of primary aldosteronism, secondary aldosteronism, hypertension, heart failure, cardiomyopathy, cardiac hypertrophy, myocardial infarction, myocardial necrosis lesion, disorder after myocardial ischemia, coronary artery disease, fibrosis or remodeling of myocardium or blood vessel, vascular restenosis, blood vessel wall thickening, arterial sclerosis, acute renal disorder, chronic kidney disease, renal fibrosis, nephropathy, hypokalemia, metabolic syndrome, obesity, sleep apnea syndrome, retinopathy, hepatic disease, idiopathic and/or cyclic edema, and sympathetic hyperactivity.

A pharmaceutical composition comprising a salt of the present invention or a crystal of the present invention as an active ingredient may be prepared by mixing a salt of the present invention or a crystal thereof with pharmaceutically acceptable additive(s) such as a diluent, a binder (for example, syrup, gum arabic, gelatin, sorbitol, tragacanth, and polyvinylpyrrolidone), an excipient (for example, lactose, sucrose, corn starch, potassium phosphate, sorbit, and glycine), a lubricant (for example, magnesium stearate, talc, polyethylene glycol, and silica), a disintegrant (for example, potato starch), and a wetting agent (for example, sodium lauryl sulfate).

The salt of the present invention, the crystal of the present invention, and pharmaceutical composition comprising the same as an active ingredient may be prepared into an appropriate dosage form such as powder, injection, tablet, capsule, and topical preparation, and then administered to a patient by using an appropriate method of administration in accordance with the dosage form such as intravenous administration, oral administration, and percutaneous administration. The term "patient" used in the present invention is an individual to be prevented or treated by the crystal of the present invention, preferably a mammal, and more preferably a human.

The dose may be determined depending on the patient's age, body weight, general health condition, sex, diet, time of administration, method of administration, excretion rate, a combination of drugs, and the severity of the disease state of the patient under treatment at the time of administration, in consideration of these or other factors. The salt of the present invention, the crystal of the present invention, and the pharmaceutical composition comprising the same as an active ingredient have low toxicity and can be safely used. The daily dose (i.e., effective amount) thereof may vary depending on the condition or body weight of the patient, the administration route, or the like. For example, in the case of parenteral administration, the salt of the present invention, the crystal of the present invention, and the pharmaceutical composition comprising the same as an active ingredient is desirably administered at a dose of approximately 0.0001 to 1000 mg/person/day, preferably approximately 0.01 to 1000 mg/person/day, and especially preferably approximately 0.01 to 500 mg/person/day, and in the case of oral administration, the salt of the present invention, the crystal of the present invention, and the pharmaceutical composition comprising the same as an active ingredient is desirably administered at a dose of approximately 0.01 to 1000 mg/person/day, preferably approximately 0.01 to 500 mg/person/day.

In the present invention, the term "prevention (or prevent)" means an action to administer the salt of the present invention, the crystal of the present invention, or the pharmaceutical composition comprising the same to an individual who has not developed an illness, a disease, or a symptom. Also, the term "treatment (or treat)" means an action to administer the salt of the present invention, the crystal of the present invention, or the pharmaceutical composition comprising the same to an individual who has already developed an illness, a disease, or a symptom. Accordingly, an action to administer the salt of the present invention, the crystal of the present invention, or the pharmaceutical composition comprising the same to an individual who has already developed an illness, a disease, or a symptom in order to prevent the deterioration, attack, or relapse of the symptom and the like is one aspect of "treatment (or treat)".

EXAMPLES

Hereinafter, the present invention is illustrated more in detail by Examples and Experimental Examples, but the present invention is not limited by them. In the present description, "equivalent(s)" means "molar equivalent(s)".

Example 1: Synthesis of Hydrobromide Form A Crystal of the Triazine Compound A

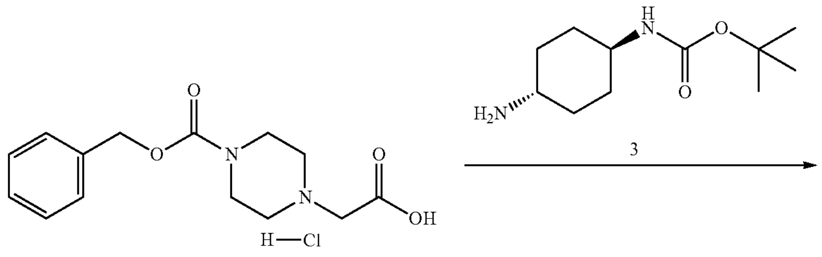

3

2

-continued
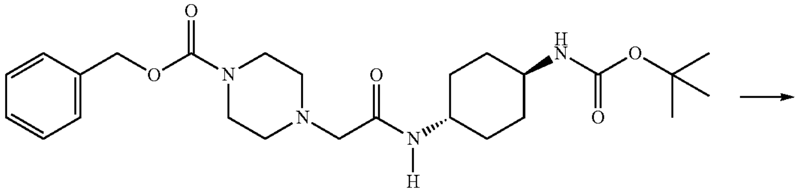
4
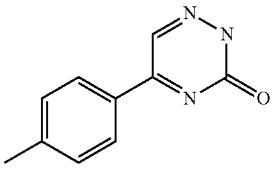
(6)
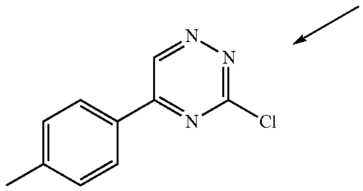
(7)
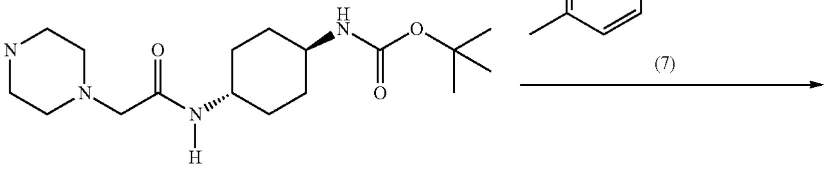
5
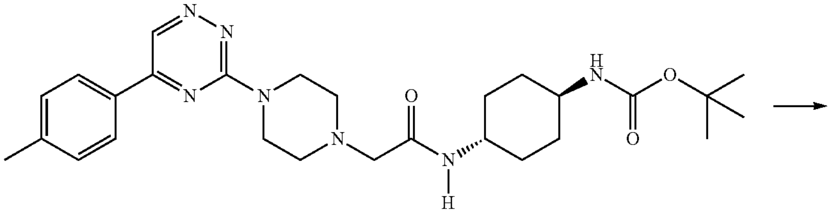
8
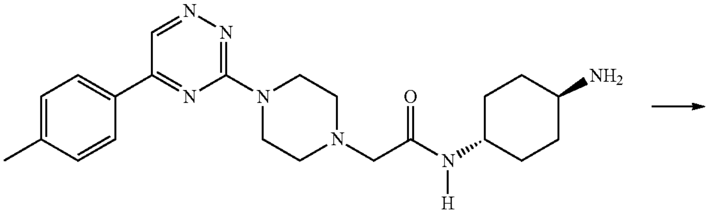
9
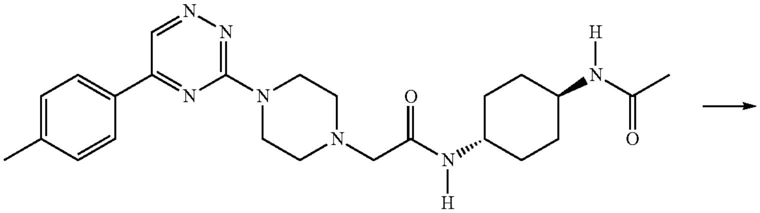
10

-continued

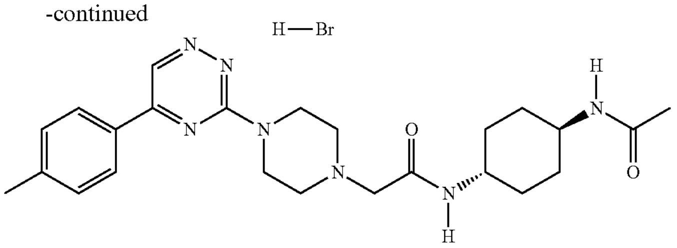

1

Under inert gas atmosphere, acetonitrile (112.30 kg), the Compound 2 (48.00 kg), diisopropylethylamine (78.80 kg), and the Compound 3 (39.20 kg) were mixed, and a solution of 50% T3P in acetonitrile was added dropwise thereto at 16 to 24° C. over 2 hours and 30 minutes. After 5 hours, a 10% aqueous solution of potassium carbonate (potassium carbonate: 38.40 kg, water: 345.6 kg) was added dropwise thereto at 19 to 22° C. over 23 minutes, then the resulting mixture was cooled to 15° C., and stirred at 9 to 15° C. for 16 hours and 30 minutes. The resulting mixture was filtered, and the resulting crystals were washed with water (240 kg). The crystals were dried under reduced pressure at 50° C. to give the Compound 4 (67.1 kg, Yield: 93%).

$^1$H NMR (DMSO-d6, 500 MHz): δ1.15-1.30 (m, 4H), 1.37 (s, 9H), 1.70-1.76 (m, 4H), 2.39 (t, J=4.6, 4H), 2.90 (s, 2H), 3.16 (br, 1H), 3.42 (br, 4H), 3.45-3.51 (m, 1H), 5.07 (s, 2H), 6.70 (d, J=7.8 Hz, 1H), 7.30-7.39 (m, 5H), 7.52 (d, J=8.2 Hz, 1H).

MS calcd for $C_{25}H_{38}N_4O_5$ 474.3, found m/z 475 $[M+H]^+$.

Under inert gas atmosphere, methanol (471.6 kg), the Compound 4 (59.7 kg), and 10% palladium carbon (6.0 kg) were mixed at 15 to 17° C., hydrogen was supplied thereto under 0.2 MPa, and the resulting mixture was stirred at 17 to 23° C. for 3 hours and 40 minutes. After the gas was replaced with inert gas, the mixture was filtered under pressure. Methanol (235.8 kg) was additionally added thereto, the resulting mixture was filtered under pressure, and the resulting filtrate was concentrated over 9 hours and 20 minutes until the volume became 180 L. Methanol (71.7 kg) was added thereto to give a solution of the Compound 5 in methanol (228.1 kg).

$^1$H NMR ($CDCl_3$, 500 MHz): δ1.19-1.30 (m, 4H), 1.44 (s, 9H), 1.97-2.04 (m, 4H), 2.46 (br, 4H), 2.89 (t, J=4.9 Hz, 4H), 2.94 (s, 2H), 3.43 (br, 1H), 3.70-3.77 (m, 1H), 4.39 (br, 1H), 6.99 (d, J=8.4 Hz, 1H).

MS calcd for $C_{17}H_{32}N_4O_3$ 340.2, found m/z 341 $[M+H]^+$.

Under inert gas atmosphere, 1,2-dimethoxyethane (237.5 kg), the Compound 6 (42.0 kg), and dimethylformamide (1.64 kg) were mixed at 15 to 16° C., and the resulting mixture was warmed to 74° C. over 1 hour. Thionyl chloride (53.4 kg) was added dropwise thereto at 73 to 79° C. over 1 hour, and the resulting mixture was stirred at 71 to 77° C. for 5 hours. After cooled to 20° C., water (210.0 L) was added dropwise thereto at 20 to 22° C. over 2 hours and 30 minutes, and the resulting mixture was stirred at 21 to 22° C. for 13 hours and 30 minutes. The resulting mixture was filtered, and the resulting crystals were washed with water (630.0 L). Under inert gas atmosphere, ethanol (99.5 kg) and the crystals were mixed at 19° C., and the resulting mixture was stirred at 19 to 21° C. for 2 hours. The resulting mixture was filtered, and the crystals were washed with ethanol (99.5 kg). The crystals were dried under reduced pressure at 30° C. to give the Compound 7 (23.7 kg, Yield: 51%).

$^1$H NMR (DMSO-d6, 500 MHz): 52.43 (s, 3H), 7.46 (d, J=7.9 Hz, 2H), 8.25 (d, J=8.3 Hz, 2H), 10.12 (s, 1H).

MS calcd for $C_{10}H_8ClN_3$ 205.0, found m/z 206 $[M+H]^+$.

Under inert gas atmosphere, to a solution of the Compound 5 in methanol was added triethylamine (23.1 kg) at 18 to 20° C., and the resulting mixture was warmed to 57° C. A solution of the Compound 7 (23.5 kg) in N-methyl-2-pyrrolidone (96.8 kg) was added dropwise thereto at 57 to 62° C., N-methyl-2-pyrrolidone (24.2 kg) was added thereto, and then the resulting mixture was stirred at 59 to 61° C. for 2 hours. Water (470.0 L) was added thereto at 54 to 58° C., the resulting mixture was stirred at 54 to 55° C. for 35 minutes, then cooled to 30° C., and the resulting mixture was stirred at 24 to 30° C. for 13 hours and 45 minutes. The resulting mixture was filtered, and the resulting crystals were washed with water (235.0 kg). The crystals were dried under reduced pressure at 50° C. to give the Compound 8 (56.6 kg, Yield: 97%).

$^1$H NMR ($CDCl_3$, 500 MHz): δ1.22-1.34 (m, 4H), 1.44 (s, 9H), 2.01-2.06 (m, 4H), 2.44 (s, 3H), 2.64 (t, J=5.2 Hz, 4H), 3.06 (s, 2H), 3.44 (br, 1H), 3.75-3.82 (m, 1H), 4.04 (br, 1H), 4.40 (br, 1H), 6.99 (d, J=8.6 Hz, 1H), 7.32 (d, J=8.0 Hz, 2H), 8.00 (d, J=8.2 Hz, 2H), 9.00 (s, 1H).

MS calcd for $C_{27}H_{39}N_7O_3$ 509.3, found m/z 510 $[M+H]^+$.

Under inert gas atmosphere, water (564.0 L) and 35% hydrochloric acid (133.1 kg) were mixed at 19 to 24° C., and the resulting mixture was warmed to 37° C. The Compound 8 (56.4 kg) was added dividedly thereto at 37 to 41° C. over 1 hour. Dilute hydrochloric acid was prepared from water (141.0 L) and 35% hydrochloric acid (33.3 kg), and added thereto at 39 to 41° C. 1 hour after the addition of the Compound 8. After the resulting mixture was stirred for 17 hours and 40 minutes from the addition of the Compound 8, the mixture was filtered under pressure at 40° C. In addition, water (112.8 L) was added thereto, and the resulting mixture was filtered under pressure. After cooled to 18° C., a 13.4 wt % aqueous solution of sodium hydroxide (480.95 kg; prepared from 48% sodium hydroxide (156.2 kg) and water (402.1 L)) was added thereto at 18 to 23° C. to adjust the pH value of the resulting solution to 11.51. After the resulting mixture was stirred at 20 to 21° C. for 45 minutes, a seed crystal of the Compound 9 (0.11 kg) was added thereto at 20° C. After stirred at 19 to 20° C. for 16 hours and 50 minutes, the resulting mixture was filtered, and the resulting crystals were washed with water (564.0 kg). The crystals were dried under reduced pressure at 50° C., and the resulting solids were crushed. The resulting product was dried under reduced pressure at 50° C. to give the Compound 9 (42.2 kg, Yield: 93%).

$^1$H NMR ($CD_3OD$, 500 MHz): δ1.22-1.41 (m, 4H), 1.92 (d, J=6.3 Hz, 4H), 2.43 (s, 3H), 2.60-2.65 (m, 5H), 3.07 (s, 2H), 3.66-3.72 (m, 1H), 4.02 (t, J=5.0 Hz, 4H), 7.36 (d, J=8.1 Hz, 2H), 8.10 (d, J=8.3 Hz, 2H), 9.06 (s, 1H).

MS calcd for $C_{22}H_{31}N_7O$ 409.3, found m/z 410 $[M+H]^+$.

Under inert gas atmosphere, methanol (55.4 kg), toluene (60.2 kg), and the Compound 9 (14.4 kg, the Compound 9 weight after moisture correction: 14.0 kg) were mixed to dissolve the Compound 9. Active carbon (0.28 kg) was added thereto, the resulting mixture was stirred at 20° C. for 1 hour and 50 minute, and then filtered under pressure. A mixed solution of methanol (22.1 kg) and toluene (25.1 kg) was additionally added thereto, and the resulting mixture was warmed to 47° C. Acetic anhydride (4.19 kg) was added thereto at 47 to 50° C., and the resulting mixture was stirred at 50 to 51° C. for 2 hours. Purified water (56.0 L) and 24% sodium hydroxide (6.8 kg) were mixed, and added to said mixture at 50° C. over 40 minutes. After the resulting mixture was stirred at 50° C. for 1 hour, it was cooled to 15° C., and stirred at 15 to 11° C. for 13 hours and 20 minutes. The resulting mixture was filtered, the resulting crystals were washed with methanol (33.2 kg), and then further washed with purified water (70.0 L). The crystals were dried under reduced pressure at 50° C. to give the Compound 10 (15.0 kg). Under nitrogen atmosphere, purified water (119.9 L), maleic acid (5.3 kg), the Compound 10 (14.8 kg), and methanol (10.5 kg) were mixed at 24° C. to dissolve the Compound 10, and then the resulting solution was pressured. Purified water (13.3 L) and methanol (1.2 kg) were additionally added thereto, the resulting mixture was warmed to 60° C., and a mixed aqueous solution of 24% sodium hydroxide (8.7 kg) and purified water (45.9 L) was added dropwise thereto at 59 to 60° C. over 50 minutes. The resulting mixture was stirred at 59 to 60° C. for 40 minutes, cooled to 25° C., and stirred at 20 to 25° C. for 14 hours and 30 minutes. The resulting mixture was filtered, and the resulting crystals were washed with purified water (74.0 L). The crystals were dried under reduced pressure at 50° C. to give the Compound (14.5 kg, Yield: 98%).

$^1$H NMR ($CDCl_3$, 500 MHz): δ1.24-1.38 (m, 4H), 1.97 (s, 3H), 2.02-2.06 (m, 4H), 2.44 (s, 3H), 2.65 (t, J=5.1 Hz, 4H), 3.06 (s, 2H), 3.76-3.83 (m, 2H), 4.04 (br, 4H), 5.32 (d, J=8.1, 1H), 7.01 (d, J=8.6 Hz, 1H), 7.32 (d, J=8.0 Hz, 2H), 8.00 (d, J=8.3 Hz, 2H), 9.00 (s, 1H).

MS calcd for $C_{24}H_{33}N_7O_2$ 451.3, found m/z 452 $[M+H]^+$.

Under nitrogen atmosphere, acetone (478.0 kg) and the Compound 10 (37.8 kg) were mixed, and the resulting mixture was warmed to 50° C. 48% Hydrobromic acid (13.9 kg), purified water (12.1 kg), and acetone (119.2 kg) were added thereto, and the resulting mixture was stirred at 46 to 50° C. for 2 hours. Acetone (150.7 kg) was additionally added thereto, and the resulting mixture was stirred at 47 to 50° C. for additional 3 hours. The mixture was cooled to 15° C., and stirred at 15° C. for 12 hours and 30 minutes. The resulting mixture was filtered, and the resulting crystals were washed with acetone (596.4 kg). The crystals were dried under reduced pressure at 50° C. for 7 hours to give the Compound 1 (hydrobromide of the Triazine compound A) (42.1 kg, Yield: 94%). In this time, the resulting crystals of hydrobromide of the Triazine compound A were Hydrobromide Form A crystals.

$^1$H NMR ($CDCl_3$, 500 MHz): δ1.24-1.38 (m, 4H), 1.97 (s, 3H), 2.02-2.06 (m, 4H), 2.44 (s, 3H), 2.66 (t, J=5.1 Hz, 4H), 3.07 (s, 2H), 3.75-3.84 (m, 2H), 4.05 (br, 4H), 5.40 (d, J=8.0, 1H), 7.02 (d, J=8.6 Hz, 1H), 7.32 (d, J=8.0 Hz, 2H), 8.00 (d, J=8.3 Hz, 2H), 9.01 (s, 1H).

MS calcd for $C_{24}H_{33}N_7O_2$ 451.3, found m/z 452 $[M+H]^+$.

The elemental analysis measurement result is shown in the following Table 1.

TABLE 1

Elemental analysis measurement result of Hydrobromide Form A crystal of the Triazine compound A

| | C | H | N | Br |
|---|---|---|---|---|
| Measured value | 53.89 | 6.39 | 18.18 | 15.17 |
| Theoretical value | 53.98 | 6.46 | 18.13 | 15.22 |

(The theoretical value represents a theoretical value when 0.1 equivalent of acetone is attached.)

<Powder X-Ray Diffraction (Hereinafter Also Referred to as XRPD) Measurement>

XRPD was measured by using a powder X-ray diffraction device X'PertPro (manufactured by PANalyical B.V.) under the following conditions.

X-ray generator: X-ray tube (Anticathode: copper, Tube voltage: 45 kv, Tube current: 40 mA)

Incidence optical system: Focusing condensing mirror

Light-receiving optical system: High-speed semiconductor array detector (X-Celerator), Extended light-receiving side arm Sample stage: HTS sample stage (oscillated at the range of 4 mm in the X-axis direction)

Cumulated number: 5 times (each incidence angle was changed by −2, −1, 0, 1, and 2°, respectively)

Measurement range: 2θ=3 to 40°

Scan speed: 0.668451°/sec

Step: 0.0167°

A XRPD result obtained from the Hydrobromide Form A crystals of the Triazine compound A is shown in FIG. 11. When the peak intensity at 25.6° as a diffraction angle expressed in 2θ is set to be 100, peaks (±0.2°, respectively) having 15 or more as the relative peak intensity are shown in the following Table 2.

TABLE 2

| 2θ (deg) | Relative intensity |
|---|---|
| 8.8 | 85 |
| 13.0 | 47 |
| 13.1 | 34 |
| 13.8 | 23 |
| 15.1 | 67 |
| 15.4 | 28 |
| 17.5 | 85 |
| 18.1 | 88 |
| 19.6 | 25 |
| 20.9 | 89 |
| 21.5 | 77 |
| 22.9 | 27 |
| 25.0 | 87 |
| 25.6 | 100 |
| 26.2 | 41 |
| 26.3 | 56 |
| 28.2 | 43 |

<Differential Scanning Calorimetry (DSC) Measurement>

DSC was measured by using a differential scanning calorimetry device X-DSC7000 (SII NanoTechnology Inc.) under the following conditions.

Rate of temperature increase: 10° C./min (30° C. to 300° C.) Atmosphere: nitrogen 100 mL/min The result obtained from Hydrobromide Form A crystals of the Triazine compound A is shown in FIG. 12. An endothermic peak was also observed at about 265 to 275° C.

<Infrared Absorption Spectrum Measurement>

A test was carried out according to potassium bromide tablet method of infrared absorption spectrum method, and the resulting infrared absorption spectra were compared.

Figure 13:
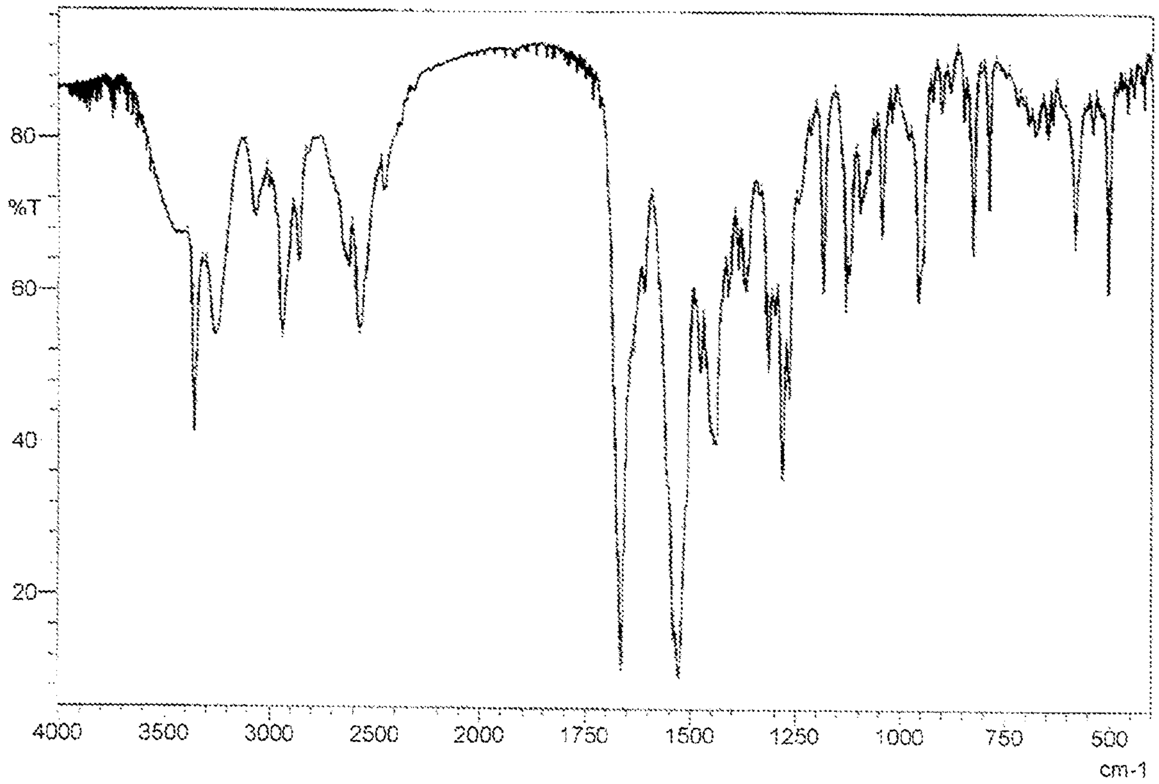
FIG. 13 is a figure showing a result of an infrared absorption spectrum measurement of Hydrobromide Form A crystal of the Triazine compound A.

A result obtained from Hydrobromide Form A crystals of the Triazine compound A is shown in FIG. 13. The assignment result of the infrared absorption spectrum is shown in the following Table 3.

TABLE 3

Assignment result of infrared absorption spectrum obtained from Hydrobromide Form A crystals of the Triazine compound A

| Wavenumber ($cm^{-1}$) | Assignment |
|---|---|
| 3360.05 | N—H stretching vibration (amide) |
| 2934.74 | C—H stretching vibration (benzene ring) |
| 2567.30 | N—H stretching vibration ($NH^+$) |
| 1663.63 | C═O stretching vibration (amide) |
| 1527.65 | C═C stretching vibration (benzene ring) |
| 824.58 | C—H out-of-plane bending vibration (1,4-disubstituted benzene) |

<Single Crystal X-Ray Diffraction Measurement>

A single crystal X-ray diffraction analysis was carried out by using a single crystal X-ray diffraction device R-AXIS RAPID/R (Rigaku Corporation) (CuKα radiation) to determine lattice constants at −40° C. and measure diffraction peak intensities, subsequently determine the phases by direct method, and carry out a structure refinement by full matrix least square method. The resulting crystallographic data and crystal structure analysis result are shown in Table 4. The reliability factor (R factor) was 12.35%, and the other several parameters also demonstrated that the present crystal structure analysis was a sufficiently highly reliable analysis result.

TABLE 4 crystallographic data and crystal structure analysis result obtained from Hydrobromide Form A crystals of the Triazine compound A

| | |
|---|---|
| Molecular formula | $C_{24}H_{33}N_7O_2$•HBr |
| Molecular weight | 532.48 |
| Lattice constant | a = 7.1256 (9) Å |
| | b = 12.360 (2) Å |
| | c = 15.286 (2) Å |
| | α = 96.489 (7)° |
| | β = 102.173 (7)° |
| | γ = 103.345 (7)° |
| | V = 1261.8 (3) $Å^3$ |
| Crystal system | Triclinic |
| Space group | P-1 |
| Z value | 2 |
| Number of unique reflections | 4522 |
| Density $D_{calc}$ | 1.401 $g/cm^3$ |
| R factor | 12.35% (I > 2.0 sigma) |

Example 2: Crystallization Study of Salt of the Triazine Compound A

Experimental Method

The Triazine compound A (about 600 mg) was dissolved into chloroform (40 mL), and each 200 μL thereof was dispensed in each vial of a 96 well plate (about 3 mg/vial). Also, regarding each acid compound, each 1 equivalent (70 μL) or 2 equivalents (140 μL) of a 0.1 moL/L solution thereof was dispensed in each vial. Regarding fumaric acid, each 140 μL of a 0.05 moL/L solution thereof was dispensed in each vial. After each solvent was allowed to evaporate by spraying nitrogen, each 300 μL of 8 kinds of solvents selected as screening solvents was dispensed in each vial, and each vial was sealed and stirred at room temperature for 4 days. Regarding the vials having precipitates, the precipitates were collected by filtration, and each XRPD thereof was measured. Regarding the vials having no precipitate, the vials were open, stored at room temperature overnight, and if solids were observed, the solids were collected by filtration, and each XRPD thereof was measured.

<Results>

Crystallization of the Triazine compound A was studied by using a mixed solvent prepared by using 18 kinds of acids and 8 kinds of solvents. As a result, novel crystals were obtained from 14 kinds of acids (hydrobromic acid, hydrochloric acid, sulfuric acid, tosic acid, mesylic acid, benzenesulfonic acid, maleic acid, citric acid, fumaric acid, tartaric acid, malic acid, succinic acid, 2-oxoglutaric acid, and glycolic acid). Crystal forms were distinguished by XRPD patterns with each other, and alphabet was assigned to crystal forms having novel XRPD patterns in the order they were found for each salt. The Hydrobromide Form A crystal of the Triazine compound A in the result of XRPD refers to the same crystal as the Hydrobromide Form A crystal of the Triazine compound A produced in Example 1.

Regarding a part of the above each crystal, thermal stability, hygroscopicity, deliquescency, and chemical stability were evaluated.

<Thermal Stability Evaluation>

Thermal stability was measured and evaluated by using a thermogravimetry/differential thermal analyzer TG/DTA7200 (SII NanoTechnology Inc.) under the following conditions.

Rate of temperature increase: 10° C./min

Range of temperature increase: 25 to 300° C.

Atmosphere: nitrogen 200 mL/min

<Hygroscopicity or Deliquescency Evaluation>

Hygroscopicity or deliquescency was evaluated as follows by using a moisture adsorption measurement device DVS-1 or DVS-intrinsic (Surface Measurement Systems Limited). Each sample (about 5 mg) was placed into an aluminum plate of which the tare weight had been corrected in advance, and the plate was hung on the precision balance of said device to precisely measure the weight at the start of measurement. The humidity was changed in a stepwise manner in a chamber at 25° C., the weight change was recorded with time, and the equilibrium weight was calculated at each humidity. On the basis of the weight at a dried condition (0% RH), the weight change rate and hydration number at each humidity were calculated.

<Chemical Stability Evaluation>

Each about 1 mg of a sample stored at 60° C. (sealed) or 60° C./75% RH (open) for 1 week and an unstored sample (at the start of test) was dissolved into a mixed solution of acetonitrile/water (1:1) (5 mL) to obtain each sample solution. A test was carried out by liquid chromatographic method under the following conditions to measure each peak area (%).

Each peak area (%) was measured by using Waters ACQUITY UPLC under the following conditions.

Detector: Photodiode array (measurement wavelength: 239 nm)

Column: Waters ACQUITY BEH C18 (2.1 mm×100 mm, 1.7 μm)

Column temperature: constant temperature about 40° C.

Mobile phase: Solution A; water/TEA (2000:1), Solution B;

Acetonitrile/TFA (2000:1)

Concentration gradient control: B % 2→100% (15 minutes)

Flow rate: 0.5 mL/min

Injection volume: 2 μL

The results are shown in Table 5.

TABLE 5

Solid physical property measurement results of crystals of salts of the Triazine compound A

| Sample | Thermal stability TG: weight change | Hygroscopicity or Deliquescency Weight change at 90% RH | Chemical stability 60° C. (sealed) | Chemical stability 60° C., 75% RH, 1 week (open) | Remarks |
|---|---|---|---|---|---|
| Hydrobromide Form A crystal | 0.9% 25-274° C. | 1.0% | −0.01% | 0.01% | 1.0 equivalent of hydrobromide |
| Hydrochloride Form A crystal | 0.4% 25-160° C. | 7.5% | −0.01% | −0.01% | 1.0 equivalent of hydrochloride |
| Hydrochloride Form B crystal | No data | 5.5% | No data | No data | 2.0 equivalents of hydrochloride |
| Sulfate Form A crystal | No data | 8% | No data | No data | 2.5 equivalents of sulfate |
| Sulfate Form B crystal | 4.3% 25-93° C. 1.6% 93-105° C. | 5%*[1] | 0% | 0.13% | 2.5 equivalents of sulfate |
| Tosilate Form B crystal | 0.7% 25° C.-melting point | 7.5% | −0.07% | −0.05% | 1.0 equivalent of tosilate |
| Tosilate Form C crystal | 1.2% 25° C.-melting point | 1.4% | 0.04% | 0.39% | 1.0 equivalent of tosilate |
| Mesilate Form A crystal | 0.8% 120° C. | 17% | −0.13% | 5.73% | 1.0 equivalent of mesilate |
| Maleate Form A crystal | 0.0% | 22% | 0.01% | 0.12% | 1.0 equivalent of maleate |
| Maleate Form B crystal | 0.4% 25-90° C. 17.6% 120-260° C. | 7.5% | 0.02% | 9.66% (deliquescent) | 1.0 equivalent of maleate |
| Citrate Form A crystal | 2.2% 25° C.-melting point | 7.6% | −0.03% | 0.03% | 1.0 equivalent of citrate |
| Malate Form A crystal | 21.2% 25-280° C. | 15% | No data | No data | 1.0 equivalent of citrate |
| Succinate Form A crystal | 0.0% 25-148° C. 23.7% 148-210° C. | 0.4% | 0.04% | 0.02% | 1.2 equivalents of succinate |
| Glycolate Form A crystal | 14.4% 70° C.-melting point | 1.9% | 0.02% | 0.02% (free body was observed at 60° C., 75% RH, 1 week) | 1.0 equivalent of glycolate |

*[1]with hydration stage

As shown in the thermal stability results in Table 5, the Hydrobromide Form A crystal, Hydrochloride Form A crystal, Sulfate Form B crystal, Tosylate Form B crystal, Tosylate Form C crystal, Mesilate Form A crystal, Maleate Form A crystal, Maleate Form B crystal, and Citrate Form A crystal did not show a significant weight change, and thus these crystal forms were confirmed to have excellent thermal stability. Further, the Succinate Form A crystal did not show a significant weight change at 25 to 148° C. (melting point), and thus said crystal form was confirmed to have excellent thermal stability.

Also, as shown in the hygroscopicity or deliquescency evaluation results in Table 5, the Hydrobromide Form A crystal, Sulfate Form B crystal, Tosylate Form B crystal, Tosylate Form C crystal, Succinate Form A crystal, and Glycolate Form A crystal did not show a significant increase of related substances, and these crystal forms were confirmed to be excellent in the reduced hygroscopicity or deliquescency. Also, the Sulfate Form B crystal had a hydration stage, and was confirmed to be a hydrate at normal temperature under relative humidity of 10 to 95%.

Further, as shown in the chemical stability test results in Table 5, the Hydrobromide Form A crystal, Hydrochloride Form A crystal, Sulfate Form B crystal, Tosylate Form B crystal, Tosylate Form C crystal, Maleate Form A crystal, Citrate Form A crystal, Succinate Form A crystal, and Glycolate Form A crystal did not show a significant increase of related substances, and these crystal forms were confirmed to have excellent chemical stability.

The Hydrobromide Form A crystal, Sulfate Form B crystal, Tosylate Form C crystal, and Succinate Form A crystal had excellent physical properties in thermal stability, hygroscopicity, deliquescency, and chemical stability.

Experimental Example 1: Synthesis of Sulfate Form B Crystal

The Triazine compound A (50 mg) was dissolved into chloroform (2 mL) at room temperature. Sulfuric acid (30 mg, 2.7 equivalents) was diluted with methanol (2 mL), and the resulting solution was added to the above solution at room temperature. The resulting mixture was stirred at room temperature for 0.5 hour, and then solvents were allowed to evaporate by nitrogen. To the resulting dried solids were added acetonitrile (3 mL) and water (100 μL) to give a syrup. To the syrup was added a seed crystal to give a suspension, and then the resulting mixture was stirred at room temperature overnight. The resulting precipitates were filtered, filtered residue was washed with acetonitrile (0.5 mL) twice, and dried under reduced pressure at 40° C. for 2.5 hours to give the Sulfate Form B crystals (75 mg, Yield: 92%, calculated as 2.5 sulfate 2 hydrate).

Experimental Example 2: Synthesis of Tosylate Form C Crystal

The Triazine compound A (50 mg) was dissolved into chloroform (2 mL) at room temperature. Tosic acid (45 mg, 2 equivalents) was dissolved into chloroform (2 mL) and methanol (0.5 mL), and the resulting solution was added to the above solution at room temperature. Solvents were allowed to evaporate by nitrogen, 1,2-dimethoxyethane (2.5 mL) was added thereto, and the resulting mixture was stirred at room temperature overnight. The resulting precipitates were filtered, and dried under reduced pressure at 40° C. for 3 hours to give the Tosylate Form C crystal (70 mg, Yield: 79%, calculated as 2 Tosylate).

Experimental Example 3: Synthesis of Succinate Form a Crystal

The Triazine compound A (40 mg) was dissolved into chloroform (2 mL) at room temperature. Succinic acid (12 mg, 1 equivalent) was dissolved into tetrahydrofuran (1 mL), and the resulting solution was added to the above solution at room temperature. After stirred for 0.5 hour, to the reaction solution was added methanol (1 mL) to give a solution, then solvents were allowed to evaporate by spraying nitrogen, toluene (2.5 mL) was added thereto, and the resulting mixture was stirred at room temperature overnight. The resulting precipitates were filtered, washed with toluene, and dried under reduced pressure at 40° C. for 2 hours to give the Succinate Form A crystal (43 mg, Yield: 85%, calculated as 1 succinate).

Experimental Example 4: Synthesis of Hydrobromide Form a Crystal (Alternative Method)

The Triazine compound A (50 mg) was dissolved into chloroform (2 mL) at room temperature. 25% Hydrobromic acid/acetic acid (39 mg) was diluted with methanol (1 mL), and the resulting mixture was added to the above solution at room temperature. After stirred at room temperature for 1 hour, solvents were allowed to evaporate by nitrogen. To the resulting dried solids was added acetonitrile (2.5 mL), and the resulting mixture was stirred at room temperature overnight. The resulting precipitates were filtered, filtered residue was washed with acetonitrile (0.5 mL) twice, and dried under reduced pressure at 40° C. for 3 hours to give the Hydrobromide Form A crystal (50 mg, Yield: 85%).

Example 3: Polymorph Search of Hydrobromide of the Triazine Compound A

Experimental Method

Hydrobromide Form A crystal of the Triazine compound A (about 500 mg) was dissolved into chloroform (5.0 mL) to give a suspension. Each 50 μL of the suspension was dispensed in each vial of a 96 well plate, solvent was dried under nitrogen stream to give solids, and then solvents shown in Table 6 were added thereto in the order of anti-solvents (6 kinds) and good-solvents (4 kinds) so that the total volume became 200 μL. As the anti-solvents, acetone, tetrahydrofuran, ethyl acetate, diisopropyl ether, acetonitrile, and toluene were selected. As the good-solvent, methanol, benzyl alcohol, N-methylpyrrolidone, and dimethylsulfoxide were selected. The plate was sealed, stirred at room temperature for 5 days, the presence or absence of suspension was visually observed, the vials containing suspensions were filtered by a 96 well filtration filter plate (MultiScreen (registered trademark) HTS+Hi-Flow, FC, Merck Millipore), and XRPD of residues on the filter were measured.

<Results>

The Hydrobromide Form A crystal of the Triazine compound A was subjected to polymorph search by using a mixed solvent prepared by using 6 kinds of anti-solvents (acetone, tetrahydrofuran, ethyl acetate, diisopropyl ether, acetonitrile, and toluene) and 4 kinds of good-solvents (methanol, benzyl alcohol, N-methylpyrrolidone, and dimethylsulfoxide). As a result of measuring each powder X-ray diffraction of resulting crystals, each crystal described in Table 6 was obtained. Crystal forms were distinguished by XRPD patterns with each other, and alphabet was assigned to crystal forms having novel XRPD patterns in the order they were found for each salt. The Hydrobromide Form A crystal of the Triazine compound A in the result of XRPD refers to the same crystal as the Hydrobromide Form A crystal of the Triazine compound A produced in Example 1.

TABLE 6

Polymorph search results 1 of crystals of hydrobromide of the Triazine compound A

| Good-solvents | Anti-solvents Acetone | Tetrahydrofuran | Ethyl acetate | Diisopropyl ether | Acetonitrile | Toluene |
|---|---|---|---|---|---|---|
| Methanol (140 μL) | A | Not applicable | Not applicable | A | Not applicable | A |
| Methanol (100 μL) | A | Not applicable | A | A | Not applicable | A |
| Methanol (60 μL) | A | A | A | A | A | A |
| Methanol (20 μL) | A | A | A | A | A | A |
| Benzyl alcohol (140 μL) | Not applicable | Amorphous | Not applicable | Not applicable | Not applicable | Not applicable |
| Benzyl alcohol (100 μL) | Amorphous | A | A | Not applicable | Not applicable | Not applicable |
| Benzyl alcohol (60 μL) | Amorphous | A | A | A | A | A |
| Benzyl alcohol (20 μL) | Amorphous | A | A | A | A | A |
| N-Methylpyrrolidone (140 μL) | Amorphous | Not applicable | A | A | Amorphous | A |
| N-Methylpyrrolidone (100 μL) | A | A | A | A | A | A |
| N-Methylpyrrolidone (60 μL) | A | A | A | A | A | A |
| N-Methylpyrrolidone (20 μL) | A | A | A | D | A | A |
| Dimethylsulfoxide (140 μL) | Not applicable | Not applicable | Not applicable | Not applicable | Not applicable | Not applicable |
| Dimethylsulfoxide (100 μL) | Not applicable | Not applicable | C | Not applicable | C | C |
| Dimethylsulfoxide (60 μL) | A | C | C | C | C | C |
| Dimethylsulfoxide (20 μL) | A | A | C | C | A | C |

Among the 96 conditions indicated in Table 6, crystal form was not changed from the Hydrobromide Form A crystal in 55 conditions, crystal form was changed from the Hydrobromide Form A crystal to the Hydrobromide Form C crystal of the Triazine compound A (dimethylsulfoxide adduct) in 11 conditions, and crystal form was changed to Hydrobromide Form D crystal of the Triazine compound A in 1 condition (N-methylpyrrolidone adduct). Here, the term of "Not applicable" means that the Triazine compound A was changed to a form of solution or the like which cannot be subjected to a powder X-ray diffraction measurement, and the term of "Amorphous" means that the Triazine compound A was changed to the Hydrobromide Form A crystal to the amorphous form. As descried above, among crystals of hydrobromide of the Triazine compound A, the Form A crystal was proved to be the most stable.

Example 4: Polymorph Search 2 of Crystals of Hydrobromide of the Triazine Compound A The polymorph search of crystals of hydrobromide of the Triazine compound A was carried out by using the Triazine compound A in acetone, water, or a mixed solvent of acetone and water, with several equivalent(s) of hydrogen bromide, or at several crystallize temperature. As a result, 11 kinds of crystal forms were produced.

Among many resulting crystal forms, the Hydrobromide Form A crystal of the Triazine compound A, Hydrobromide Form F crystal of the Triazine compound A, and Hydrobromide Form N crystal of the Triazine compound A had excellent physical properties in thermal stability, hygroscopicity, deliquescency, and chemical stability.

The crystallization conditions of the Hydrobromide Form A crystal of the Triazine compound A, Hydrobromide Form F crystal of the Triazine compound A, and Hydrobromide Form N crystal of the Triazine compound A having appropriate physical properties for producing a medicament are shown in Table 7. The XRPD measurement device and measurement conditions are the same as used in Example 1. The Hydrobromide Form A crystal of the Triazine compound A in the result of XRPD refers to the same crystal as the Hydrobromide Form A crystal of the Triazine compound A produced in Example 1.

TABLE 7

| Crystallization method of crystals of hydrobromide of the Triazine compound A | | | | | | |
|---|---|---|---|---|---|---|
| Experiment | Material | Hydrogen bromide (equivalent) | Solvent | Temperature | Crystal form | Equivalent(s) of hydrobromide |
| (a) | Triazine compound A | hydrogen bromide (1.0 equivalent) | acetone/water | 50° C. | Hydrobromide Form A crystal | 1.0 equivalent |
| (b) | Triazine compound A | hydrogen bromide (2.1 equivalents) | acetone/water | 50° C. | Hydrobromide Form F crystal | 2.0 equivalents |
| (c) | Triazine compound A | hydrogen bromide (1.4 equivalents) | water | 50° C. | Hydrobromide Form N crystal | 1.0 equivalent |

In the method (a), the Hydrobromide Form A crystal of the Triazine compound A was produced. This crystal was proved to comprise 1.0 equivalent of hydrobromic acid.

In the method (b), the Hydrobromide Form F crystal of the Triazine compound A was produced. This crystal was proved to comprise 2.0 equivalents of hydrobromic acid.

In the method (c), the Hydrobromide Form N crystal of the Triazine compound A was produced. This crystal was proved to comprise 1.0 equivalent of hydrobromic acid.

Experimental Example 5

Experimental Example of Method (a)

Crystals were produced according to the crystallization method described in Example 1.

Experimental Example 6

Experimental Example of Method (b)

The Triazine compound A (10.0 g) was suspended in acetone (300 mL) at 50° C., then a 48% aqueous solution of hydrobromic acid (7.84 g, 2.1 equivalents) was added thereto, and the resulting mixture was stirred for about 20 hours. The mixture was cooled to 10° C., and filtered. The resulting wet body was washed with acetone (50 mL), and dried under reduced pressure at 40° C. for 24 hours to give the Hydrobromide Form F crystal (13.45 g).

Experimental Example 7

Experimental Example of Method (c)

The Triazine compound A (50.0 g) was suspended in water (450 mL) at 50° C., then a 48% aqueous solution of hydrobromic acid (26.19 g, 1.4 equivalents) was added thereto, and the resulting mixture was stirred for about 5 hours. The mixture was cooled to 14° C., and filtered. The resulting wet body was washed with acetone (200 mL), and draught drying was carried out for 21 hours to give the Hydrobromide Form N crystal (57.43 g).

Example 5: Comparison of Hydrobromide Form a Crystal of the Triazine Compound a, Hydrobromide Form F Crystal of the Triazine Compound a, and Hydrobromide Form N Crystal of the Triazine Compound A In the following Comparative test results, the "Hydrobromide Form A crystal of the Triazine compound A" refers to results of crystals obtained from the method described in Example 1.

In the following Comparative test results, the "Hydrobromide Form F crystal of the Triazine compound A" refers to results of crystals obtained from the method described in Experimental Example 6.

In the following Comparative test results, the "Hydrobromide Form N crystal of the Triazine compound A" refers to results of crystals obtained from the method described in Experimental Example 7.

The powder X-ray diffraction measurement results obtained from the above Hydrobromide Form F crystal and Hydrobromide Form N crystal of the Triazine compound A are shown below.

<Powder X-Ray Diffraction Measurement>

XRPD was measured by using a powder X-ray diffraction device X'PertPro (manufactured by PANalyical B.V.) under the following conditions.

X-ray generator: X-ray tube (Anticathode: copper, Tube voltage: 45 kv, Tube current: 40 mA)

Incidence optical system: Focusing condensing mirror

Light-receiving optical system: High-speed semiconductor array detector (X-Celerator), Extended light-receiving side arm Sample stage: HTS sample stage (oscillated at the range of 4 mm in the X-axis direction)

Cumulated number: 5 times (each incidence angle was changed by −2, −1, 0, 1, and 2°, respectively)

Measurement range: 2θ=3 to 40°

Scan speed: 0.668451°/sec

Step: 0.0167°

Figure 7:
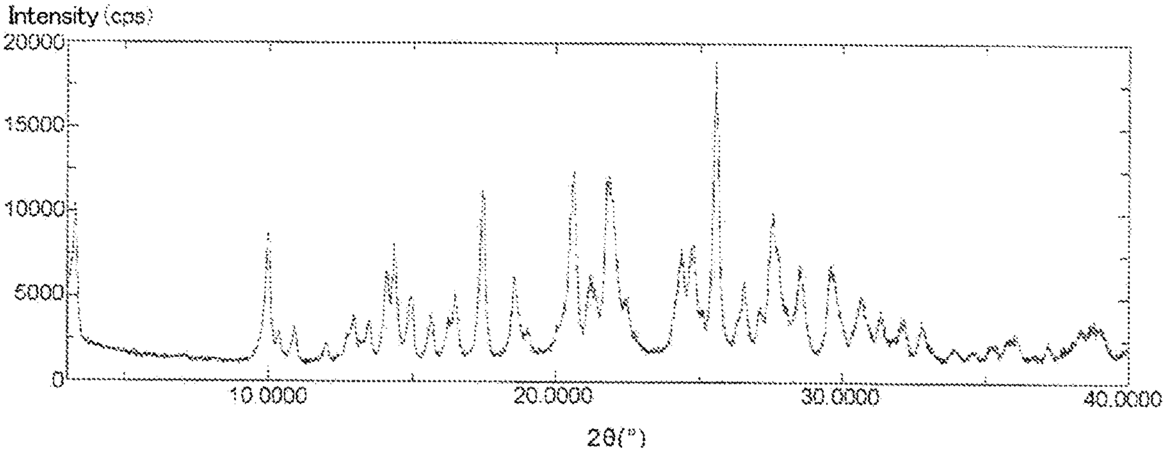
FIG. 7 is a figure showing a result of a powder X-ray diffraction measurement of Hydrobromide Form F crystals of the Triazine compound A.
Figure 8:
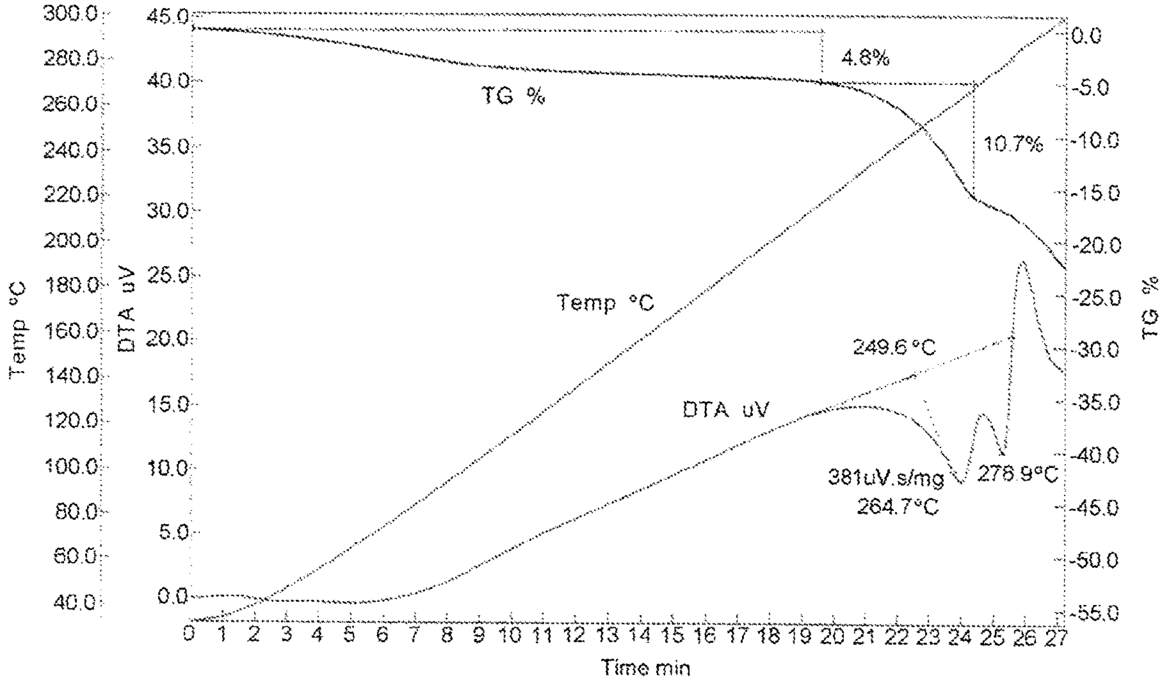
FIG. 8 is a figure showing a result of differential scanning calorimetry of Hydrobromide Form F crystals of the Triazine compound A.

A XRPD result obtained from the Hydrobromide Form F crystals of the Triazine compound A is shown in FIG. 7. The peaks (±0.2°, respectively) are shown in the following Table 8.

TABLE 8

| 2θ (deg) |
|---|
| 3.3 |
| 10.0 |
| 14.1 |
| 14.4 |
| 14.9 |
| 16.5 |
| 17.4 |
| 18.5 |
| 20.6 |
| 21.2 |
| 21.8 |
| 24.3 |
| 24.7 |
| 25.6 |
| 27.5 |

TABLE 8-continued

| 2θ (deg) |
|---|
| 28.5 |
| 29.6 |

The characteristic peaks in the powder X-ray diffraction pattern of the Form F crystals include 10.0°±0.2° and 27.5°±0.2° as diffraction angles expressed in 2θ. In one embodiment, the Form F crystals have further peaks at 3.3°±0.2° and 14.4°±0.2° as diffraction angles expressed in 2θ in the powder X-ray diffraction pattern. Other characteristic peaks thereof include 17.4°±0.2°, 20.6°±0.2°, 21.8°±0.2°, and 25.6°±0.2°. Still other characteristic peaks thereof include 14.1°±0.2°, 14.9°±0.2°, 16.5±0.2°, 18.5±0.2°, 21.2°±0.2°, 24.3±0.2°, 24.7°±0.2°, 28.5°±0.2°, and 29.6°±0.2°. The Hydrobromide Form F crystal of the Triazine compound A is a crystal having substantially the same powder X-ray diffraction pattern as FIG. 7.

Figure 9:
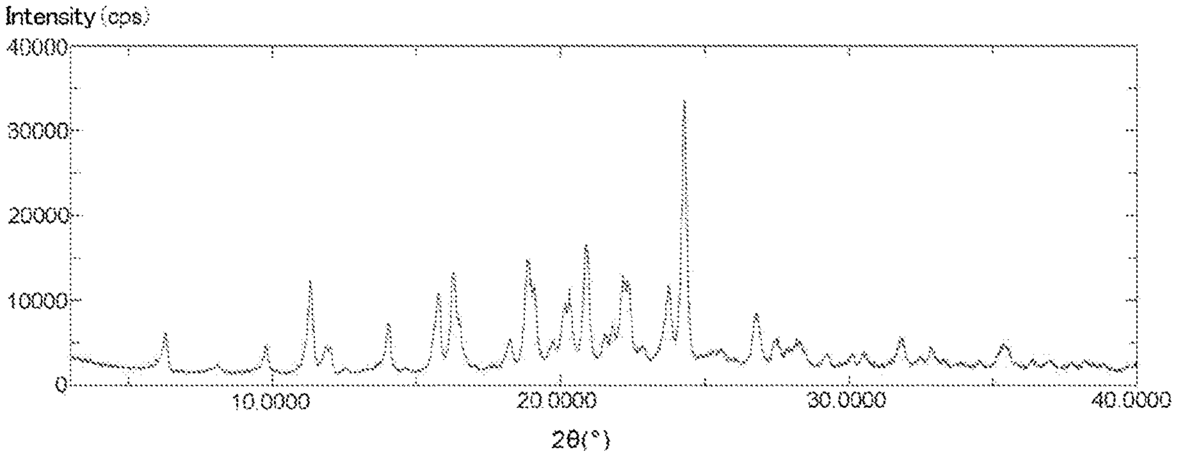
FIG. 9 is a figure showing a result of a powder X-ray diffraction measurement of Hydrobromide Form N crystals of the Triazine compound A.
Figure 10:
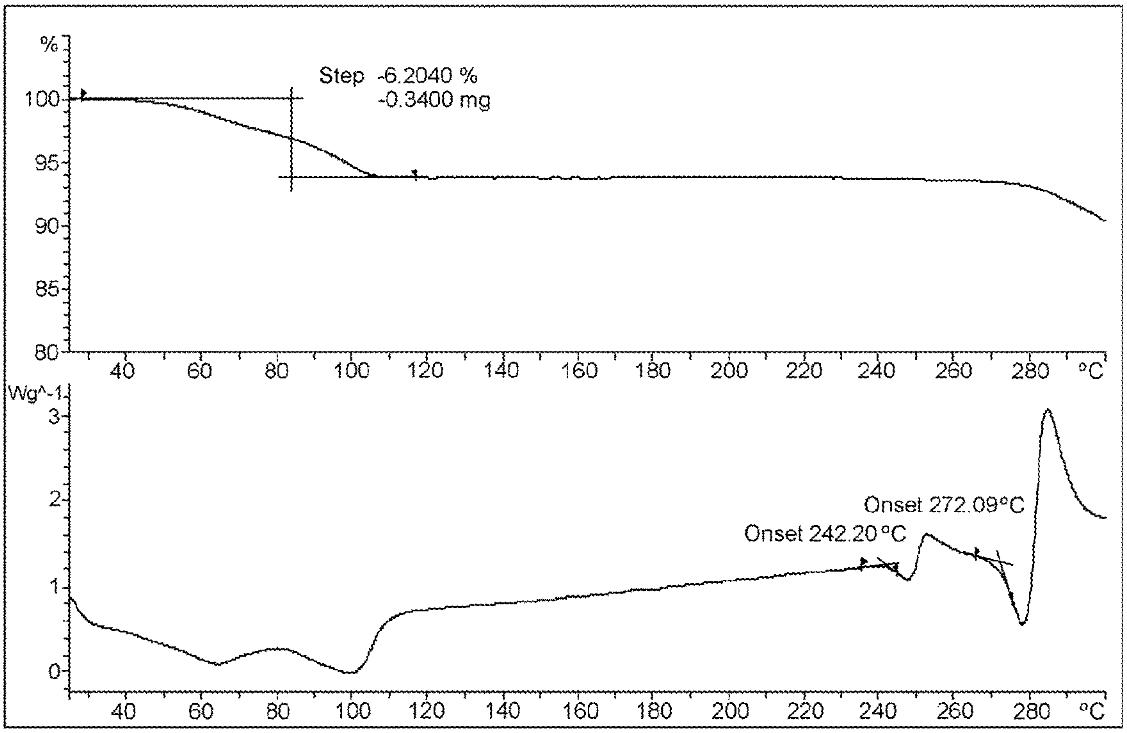
FIG. 10 is a figure showing a result of differential scanning calorimetry of Hydrobromide Form N crystals of the Triazine compound A.

The XRPD result of the Hydrobromide Form N crystals of the Triazine compound A is shown in FIG. 9. The peaks (±0.2°, respectively) are shown in the following Table 9.

TABLE 9

| 2θ (deg) |
|---|
| 6.2 |
| 9.8 |
| 11.3 |
| 11.9 |
| 14.0 |
| 15.6 |
| 16.2 |
| 18.8 |
| 19.1 |
| 20.4 |
| 20.9 |
| 22.1 |
| 22.4 |
| 23.8 |
| 24.3 |
| 26.8 |
| 31.9 |

The characteristic peaks in the powder X-ray diffraction pattern of the Form N crystals include 11.3°±0.2° and 24.3°±0.2° as diffraction angles expressed in 2θ. In one embodiment, the Form N crystals further have peaks at 6.2°±0.2° and 31.9°±0.2° as diffraction angles expressed in 2θ in the powder X-ray diffraction pattern. Other characteristic peaks thereof include 11.9°±0.2°, 22.4°±0.2°, 23.8°±0.2°, and 26.8°±0.2°. Still other characteristic peaks thereof include 9.8°±0.2°, 14.0°±0.2°, 15.6°±0.2°, 16.2°±0.2°, 18.8°±0.2°, 19.1°±0.2°, 20.4°±0.2°, 20.9°±0.2°, and 22.1°±0.2°. The Hydrobromide Form N crystal of the Triazine compound A is a crystal having substantially the same powder X-ray diffraction pattern as FIG. 9.

The above each crystal was evaluated for thermal stability, hygroscopicity, deliquescency, and chemical stability.

<Thermal Stability Evaluation>

Thermal stability was measured and evaluated by using a thermogravimetry/differential thermal analyzer TG/DTA7200 (SII NanoTechnology Inc.) under the following conditions Rate of temperature increase: 10° C./min Range of temperature increase: 30 to 300° C.

Atmosphere: nitrogen 200 mL/min or using a TGA/DSC1 thermogravimetric analyzer (manufactured by Mettler Toledo, STARe system) under the following conditions.

Rate of temperature increase: 10° C./min

Range of temperature increase: 25 to 300° C.

Atmosphere: nitrogen 50 mL/min

<Hygroscopicity or Deliquescency Evaluation>

Hygroscopicity or deliquescency was evaluated as follows by using a moisture adsorption measurement device DVS-1 or DVS-intrinsic (Surface Measurement Systems Limited). Each sample was placed into a cell of which the tare weight had been corrected in advance, and the cell was hung on the precision balance of said device to precisely measure the weight at the start of measurement. The humidity was changed in a stepwise manner, the weight change was recorded with time, and the equilibrium weight was calculated at each humidity. On the basis of the weight of anhydride converted from the amount of water at a dried condition (0% RH) or at the start of measurement observed by an alternative method, the weight change rate at each humidity was calculated.

<Chemical Stability Evaluation>

Each sample was stored at 60° C. under a sealed condition and at 60° C. under 75% RH for 1 week, and an increase or decrease of related substance(s) after the storage was calculated by high-performance liquid chromatographic method on the basis of the area percentage of each peak. Also, the condition of each sample after the storage was observed.

The results are shown in Table 10.

TABLE 10

| Sample | Thermal stability TG: weight change | Hygroscopicity or Deliquescency Weight change at 90% RH | Chemical stability 60° C. (sealed) | Chemical stability 60° C., 75% RH, 1 week (open) | Remarks |
|---|---|---|---|---|---|
| Hydrobromide Form A crystal | 0.98 25-274° C. | 1.0% | −0.01% | 0.01% | comprising 1.0 equivalent of hydrobromic acid |
| Hydrobromide Form F crystal | 4.8% room temperature-200° C. | 3.5%*[1] | 0.02% | 0.12% | comprising 2.0 equivalents of hydrobromic acid |
| Hydrobromide Form N crystal | 6.2% 25-242° C. | 7.2%*[1] | No data | 0.00% | comprising 1.0 equivalent of hydrobromic acid |

*[1]with hydration stage

Among the resulting many crystal forms, the Hydrobromide Form A crystal, Hydrobromide Form F crystal, and Hydrobromide Form N crystal had excellent physical properties in thermal stability, hygroscopicity, deliquescency, and chemical stability. Also, the Hydrobromide Form F crystal and Hydrobromide Form N crystal had a hydration stage, and thus were confirmed to be hydrate at normal temperature under relative humidity of 10 to 95%.

Example 6: Effect of Water at the Crystallization of Hydrobromide Form a Crystal

TABLE 11

| Entry | Water content | Stirring hour(s) 1 hour | 19 hours | 45 hours | Mix rate of the Triazine compound A in mother liquor |
|---|---|---|---|---|---|
| 1 | 0.64% | Form F crystal<br>Form A crystal<br>Triazine compound A | Form F crystal<br>Form A crystal<br>Triazine compound A | Form A crystal | 0.2% |
| 2 | 2.0% | Form A crystal | Form A crystal | Form A crystal | 0.6% |
| 3 | 2.5% | Form A crystal | Form A crystal | Form A crystal | 0.6% |
| 4 | 3.0% | Form A crystal | Form A crystal | Form A crystal | 1.1% |
| 5 | 5.0% | Form A crystal | Form A crystal | Form A crystal | 5.5% |

Experimental Method

The Triazine compound A was added to mixed solvents of acetone and water having several water contents, an aqueous solution of hydrobromic acid (1 equivalent) was added thereto, and the resulting mixture was stirred at 50° C. After 1 hour, 19 hours, and 45 hours from the start of stirring, a part of the reaction solution was collected by filtration, and the filtered residue was subjected to a powder X-ray diffraction measurement. The transition rates to the Form A crystal in the mixed solvents of acetone and water having several water contents were confirmed.

<Results>

The results are shown in Table 11.

In the mixed solvent having the water content of 0.64% (Entry 1), a mixture of the Hydrobromide Form A crystal, the Hydrobromide Form F crystal, and the Triazine compound A was obtained after 19 hours from the start of stirring, while the crystals converged on the Hydrobromide Form A crystals after 45 hours from the start of stirring.

In the mixed solvents having water contents of 2 to 5% (Entries 2 to 5), crystals converged on the Hydrobromide Form A crystals after 1 hour from the start of stirring. Further, in the water contents of 2 to 3%, the mix rates of the Triazine compound A in the mother liquors were excellent (0.6 to 1.1%), while in the water content of 5%, the mix rate of the Triazine compound A in the mother liquor was confirmed to increase (5.5%).

It was confirmed that the Hydrobromide Form A crystals may be obtained in short stirring hour(s) at a high recovery rate by adding the Triazine compound A to a mixed solvent of acetone and water having water content of 2.0 to 3.0%, adding an aqueous solution of hydrobromic acid (1 equivalent) thereto, and stirring the resulting mixture at 50° C. This method is an industrially advantageous crystallization method of a medicament.

Example 7: Comparison of Pharmacokinetics of the Triazine Compound a with Pharmacokinetics of the Hydrobromide of the Triazine Compound a at the Combined Use with a Promotor of Gastric Acid Secretion or an Inhibitor of Gastric Acid Secretion

Experimental Method

The pharmacokinetics of hydrobromide of the Triazine compound A and the Triazine compound A under gastric acid secretion and gastric pH adjustment was evaluated by using dogs treated with a promotor of gastric acid secretion or an inhibitor of gastric acid secretion according to a crossover method of 2 groups with 4 phases.

Pentagastrin was used in the treatment of a promotor of gastric acid secretion. Pentagastrin (2.8 mg) was dissolved into dimethylsulfoxide (7.0 mL) and water for injection (7.0 mL) to prepare an administration solution, and administered into a muscle in the thigh at a dose of 10 μg/0.05 mL/kg. Pentagastrin was administered 0.5 hour before and 0.5 hour after the administration of each test material (hydrobromide of the Triazine compound A (Compound 1 prepared in Example 1) or the Triazine compound A (Compound 10 prepared in Example 1)). Omeprazole was used in the treatment of an inhibitor of gastric acid secretion. Omeprazole (90 mg) was dissolved into a 1:1 mixed solution (22.5 mL) of a 0.1% aqueous solution of sodium hydrogen carbonate (w/v) and polyethyleneglycol 400 to prepare an administration solution, and administered into a saphenous vein of the hind limb at a dose of 1 mg/0.25 mL/kg. Omeprazole was administered 1 hour before the administration of each test material.

After 25 mL of water for injection was administered to each dog by using a syringe having an oral catheter, the hydrobromide of the Triazine compound A or the Triazine compound A was forcedly orally administered to each dog at a dose of 10 mg/capsule (in case of hydrobromide of the Triazine compound A, free form equivalent (i.e., 10 mg in terms of the Triazine compound A)), and additional 25 mL of water for injection was administered to each dog through the syringe having an oral catheter. Each test material was administered under fasting state, and each dog was fed 6 hours after the administration. Each dog was deprived of water from 1 hour before the administration of each test material to 2 hours after the administration.

Tests were carried out by using 6 heads of 4 year-old male beagle and dividing them into two groups, each of which comprises 3 heads. The dogs in Group 1 were subjected to the administration in the order of (Phase 1) omeprazole administration, then the Triazine compound A administration, (Phase 2) omeprazole administration, then the hydrobromide of the Triazine compound A administration, (Phase 3) pentagastrin administration, then the Triazine compound A administration, and (Phase 4) pentagastrin administration, then the hydrobromide of the Triazine compound A administration, and the dogs in Group 2 were subjected to the administration in the order of (Phase 1) omeprazole administration, then the hydrobromide of the Triazine compound A administration, (Phase 2) omeprazole administration, then the Triazine compound A administration, (Phase 3) pentagastrin administration, then the hydrobromide of the Triazine compound A administration, and (Phase 4) pentagastrin administration, then the Triazine compound A administration, and washout period between each phase was 6 or 7 days. After 15 minutes, 30 minutes, 1, 2, 4, 6, 8, and 24 hour(s) from the administration of the hydrobromide of the Triazine compound A or the Triazine compound A, 0.6 mL of whole blood sample was collected under awakening of each dog from a cephalic vein by using a heparin sodium injection. The whole blood sample was processed into a plasma, and the drug concentration of the Triazine compound A was analyzed by using liquid chromatography-tandem mass spectrometry (LC-MS/MS). The area under the plasma concentration-time curve (AUC; area from time 0 to time at which the final concentration can be measured is $AUC_{0-t}$ and area from time 0 to infinite time calculated by the extrapolation of the final elimination phase is $AUC_{0-\infty}$) on the basis of plasma vs. time data, maximum plasma concentration ($C_{max}$), time to maximum plasma concentration ($T_{max}$), and elimination half-life from plasma ($T_{1/2}$) were calculated by using Phoenix WinNonlin Software Ver.6.3 (Certara L.P.).

<Results>

Figure 14:
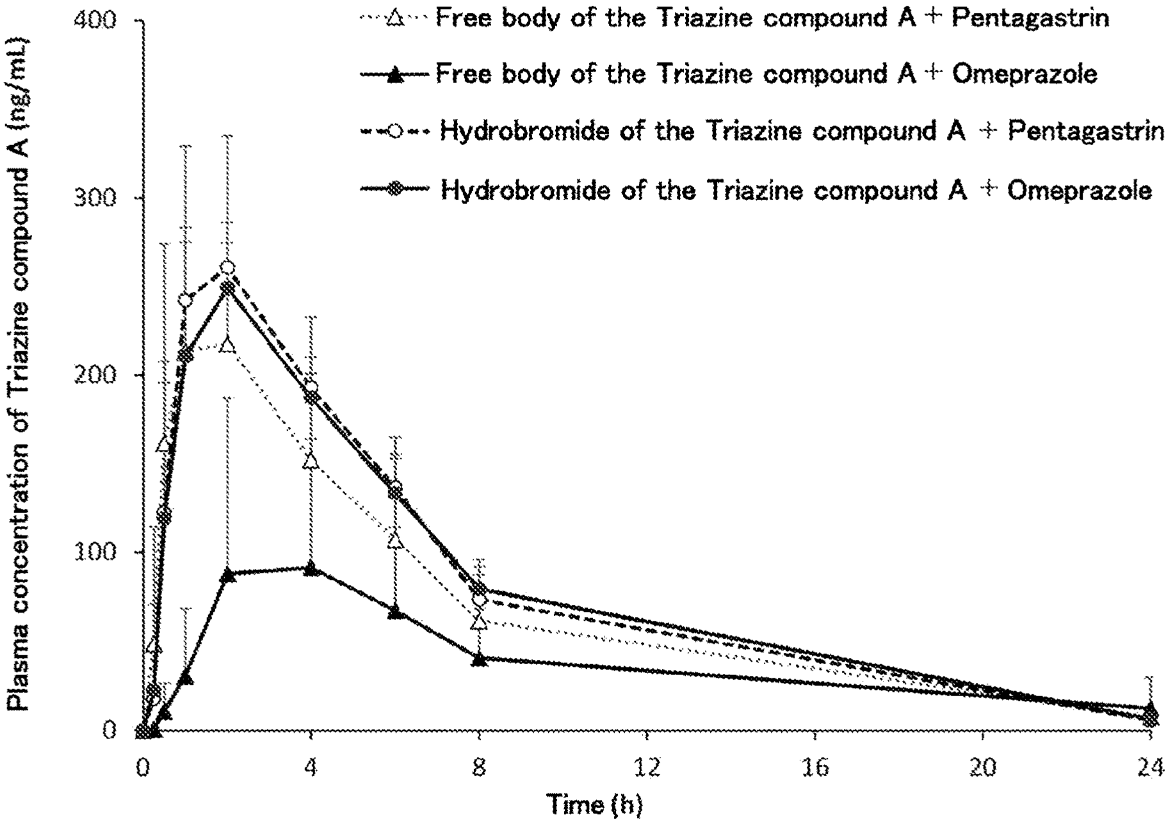
FIG. 14 is a figure showing pharmacokinetics of a free body of the Triazine compound A and hydrobromide of the Triazine compound A under a condition comprising pentagastrin which is a promotor of gastric acid secretion or omeprazole which is an inhibitor of gastric acid secretion.

The results are shown in Table 12 and FIG. 14.

TABLE 12

| Administered test material | Combined drug Treatment condition | | Pharmacokinetics parameter $C_{max}$ (ng/mL) | $T_{max}$ (h) | $T_{1/2}$ (h) | $AUC_{0-t}$ (ng · h/mL) | $AUC_{0-\infty}$ (ng · h/mL) |
|---|---|---|---|---|---|---|---|
| Triazine compound A | Pentagastrin Increased gastric acid secretion | mean | 222.3 | 1.42 | 4.26 | 1694.0 | 1909.1 |
| | | SD | 121.1 | 0.66 | 0.40 | 882.9 | 879.4 |
| | | CV (%) | 54.5 | 46.9 | 9.3 | 52.1 | 46.1 |
| | Omeprazole Reduced gastric acid secretion | mean | 102.3 | 3.33 | 5.60 | 942.7 | 999.8 |
| | | SD | 91.3 | 1.03 | 1.95 | 661.7 | 785.3 |
| | | CV (%) | 89.3 | 31.0 | 34.8 | 70.2 | 78.5 |
| Hydrobromide of Triazine compound A | Pentagastrin Increased gastric acid secretion | mean | 262.9 | 1.67 | 4.24 | 1989.1 | 2024.3 |
| | | SD | 25.8 | 0.52 | 0.41 | 191.0 | 186.3 |
| | | CV (%) | 9.8 | 31.0 | 9.7 | 9.6 | 9.2 |
| | Omeprazole Reduced gastric acid secretion | mean | 256.1 | 1.83 | 4.30 | 1989.2 | 2030.2 |
| | | SD | 34.1 | 0.41 | 0.55 | 169.0 | 166.0 |
| | | CV (%) | 13.3 | 22.3 | 12.9 | 8.5 | 8.2 |

It was confirmed that the absorption of the Triazine compound A was reduced under the reduced gastric acid conditions, and both $C_{max}$ and AUC were reduced by about 50% as compared to the increased gastric acid secretion conditions. Also, under the reduced gastric acid conditions, CV (%) was great, which suggested that individual difference would likely to generate. Regarding the hydrobromide of the Triazine compound A, the plasma concentration was not changed regardless of the gastric acid conditions, and was confirmed not to be affected by gastric pH.

The crystal form of the hydrobromide of the Triazine compound A used in Example 7 was the Hydrobromide Form A crystal.

Experimental Example 8: Aldosterone Synthase (Hereinafter Referred to as CYP11B2) Inhibitory Activity Measurement Experimental Method The pcDNA3.1-human CYP11B2 plasmid was transfected into a Chinese hamster lung fibroblast V79 cell line to produce a cell line stably expressing a human CYP11B2 gene.

The cells were cultured and grown in the Dulbecco's modified Eagle's/Ham's medium supplemented with 10% fetal bovine serum and 1% G418 disulfate solution under the environment of 37° C., 95% air, and 5% $CO_2$, and the grown cells were harvested.

Then, the cells were fractionated to obtain mitochondria by reference to a method described in Chabre et al. JCE & M 85 (11) 4060-68, 2000. In particular, the cells suspended in a 5 mmol/L Tris-HCl buffer (pH 7.4) containing 250 mmol/L sucrose were homogenized in a Teflon (registered trademark) Potter Elvehjem homogenizer, and then the suspension was centrifuged (800×g, 15 min). The supernatant was separated and again centrifuged (10000×g, 15 min) to obtain a pellet (mitochondrial fraction).

The mitochondrial fraction diluted with a buffer containing 10 mmol/L $KH_2PO_4$, 10 mmol/L Tris, 20 mmol/L KCl, 25 mmol/L sucrose, 5 mmol/L $MgCl_2$, and 0.05% bovine serum albumin was dispensed to a 96 well plate. 0.5 μmol/L Deoxycorticosterone and 150 μmol/L NADPH were added to each well, and incubated for 1.5 to 2 hours at room temperature to produce aldosterone. The amount of the produced aldosterone in the incubated solution was determined by using HTRF (Homogeneous Time Resolved Fluorescence) method.

$IC_{50}$ (nmol/L) was calculated by analyzing the aldosterone production inhibition rate (%) of each concentration of the Triazine compound A of the present invention by non-linear regression to a logistic curve.

As a result, the Triazine compound A of the present invention had 9.0 nmol/L as $IC_{50}$, and thus the Triazine compound A of the present invention had a potent aldosterone synthase inhibitory activity.

Also, the same Experiments as the present Experimental Example can be carried out by using the salts of the Triazine compound A of the present inventions and the crystals thereof to confirm that the salts of the Triazine compound A of the present invention and the crystals thereof have similarly potent aldosterone synthase inhibitory activities.

INDUSTRIAL APPLICABILITY

The novel salts of 3-[4-[[trans-4-(acetamino)cyclohexyl] carbamoylmethyl]piperazin-1-yl]-5-(p-tolyl)-1,2,4-triazine are salts to produce excellent crystals, and especially, hydrobromide thereof shows stable pharmacokinetics under both increased gastric acid secretion and reduced gastric acid secretion, and are salts that do not comprise compounds which may have adverse effects on living bodies in terms of safety. Also, novel crystals of salts of 3-[4-[[trans-4-(acetamino)cyclohexyl]carbamoylmethyl]piperazin-1-yl]-5-(p-tolyl)-1,2,4-triazine comprise no residual solvent used in the crystallization, have excellent thermal stability, are stable under humid conditions with reduced weight change, are not deliquescent, have excellent chemical stability, have excellent safety, and comprise no compound that may have adverse effects on living bodies in terms of safety, and further, said crystals can be produced by a reproducibly industrially appropriate method, and thus are excellent crystals as active pharmaceutical ingredients.

Further, the method for producing crystals of 3-[4-[[trans-4-(acetamino)cyclohexyl]carbamoylmethyl]piperazin-1-yl]-5-(p-tolyl)-1,2,4-triazine is an industrially advantageous method which does not use production intermediate compounds having an explosive risk and a genotoxic risk, can produce the active pharmaceutical ingredient at a high yield, and can reproducibly produce the most stable crystals at a high yield.

The invention claimed is:

1. A crystal of pharmaceutically acceptable salt of 3-[4-[[trans-4-(acetamino)cyclohexyl]carbamoylmethyl]piperazin-1-yl]-5-(p-tolyl)-1,2,4-triazine, wherein the salt is hydrobromide, sulfate, succinate, or tosylate.

2. The crystal according to claim 1, wherein the salt is hydrobromide.

3. The crystal according to claim 2, having peaks at 8.8° 0.2°, 18.1°±0.2°, 20.9°±0.2°, and 25.6°±0.2° as diffraction angles expressed in 2θ in a powder X-ray diffraction spectrum.

4. The crystal according to claim 2, having an endothermic peak at 265 to 275° C. in a differential scanning calorimetry analysis.

5. An aldosterone synthase inhibitor comprising the crystal according to claim 1 as an active ingredient.

6. A pharmaceutical composition comprising the crystal according to claim 1 and a pharmaceutically acceptable additive.

7. An aldosterone synthase inhibitor comprising the crystal according to claim 2 as an active ingredient.

8. A pharmaceutical composition comprising the crystal according to claim 2 and a pharmaceutically acceptable additive.

9. An aldosterone synthase inhibitor comprising the crystal according to claim 3 as an active ingredient.

10. A pharmaceutical composition comprising the crystal according to claim 3 and a pharmaceutically acceptable additive.

11. An aldosterone synthase inhibitor comprising the crystal according to claim 4 as an active ingredient.

12. A pharmaceutical composition comprising the crystal according to claim 4 and a pharmaceutically acceptable additive.

13. The crystal according to claim 3 further having peaks at 15.1°±0.2°, 17.5°±0.2°, 21.5°±0.2°, and 25.0°±0.2° as diffraction angles expressed in 2θ in a powder X-ray diffraction spectrum.

14. An aldosterone synthase inhibitor comprising the crystal according to claim 13 as an active ingredient.

15. A pharmaceutical composition comprising the crystal according to claim 14 and a pharmaceutically acceptable additive.

* * * * *